(12) United States Patent
Mohapatra et al.

(10) Patent No.: US 11,884,906 B1
(45) Date of Patent: Jan. 30, 2024

(54) 4D-PERFUSED TUMOROID-ON-A-CHIP PLATFORM FOR PERSONALIZED CANCER TREATMENT APPLICATIONS

(71) Applicant: University of South Florida, Tampa, FL (US)

(72) Inventors: Subhra Mohapatra, Lutz, FL (US); Shyam S. Mohapatra, Lutz, FL (US); Tao Wang, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 18/116,550

(22) Filed: Mar. 2, 2023

Related U.S. Application Data

(62) Division of application No. 16/799,413, filed on Feb. 24, 2020, now Pat. No. 11,685,885.

(60) Provisional application No. 62/809,305, filed on Feb. 22, 2019.

(51) Int. Cl.
*C12M 3/06* (2006.01)
*B01L 3/00* (2006.01)
*C12M 1/32* (2006.01)
*C12M 1/12* (2006.01)
*G01N 33/50* (2006.01)
*C12M 1/34* (2006.01)
*C12N 5/09* (2010.01)

(52) U.S. Cl.
CPC ....... *C12M 23/16* (2013.01); *B01L 3/502715* (2013.01); *C12M 23/12* (2013.01); *C12M 25/14* (2013.01); *C12M 41/26* (2013.01); *C12M 41/36* (2013.01); *C12N 5/0693* (2013.01); *G01N 33/5011* (2013.01); *B01L 2300/0627* (2013.01); *B01L 2300/0819* (2013.01); *B01L 2300/0829* (2013.01); *C12N 2503/02* (2013.01); *C12N 2513/00* (2013.01)

(58) Field of Classification Search
CPC ...... C12M 23/16; C12M 23/12; C12M 25/14; C12M 41/26; C12M 41/36; C12N 5/0693; C12N 2503/02; C12N 2513/00; B01L 2300/0627; B01L 2300/0819; B01L 2300/0829; G01N 33/5011
See application file for complete search history.

(56) References Cited

U.S. PATENT DOCUMENTS

2012/0003732 A1\* 1/2012 Hung ..................... C12M 23/40
435/289.1

\* cited by examiner

*Primary Examiner* — Michael L Hobbs
(74) *Attorney, Agent, or Firm* — Michele L. Lawson; Smith & Hopen, P.A.

(57) ABSTRACT

A 4D-perfused tumoroid-on-a-chip platform used in personalized cancer treatment. The platform includes a plate with a plurality of bottomless wells that resides atop a microfluidic channel layer, which in turn resides atop a surface acoustic wave (SAW) based sensor layer that is capable of measuring potential pH values of fluids disposed within the platform. The microfluidic channel layer includes a plurality of bioreactors, with each bioreactor including an inlet well, a culture well, and an outlet well. The inlet well, culture well, and outlet well form a closed system via fluid conduits spanning from the inlet well to the culture well, as well as from the culture well to the outlet well. Due to the fluid flow from the plate to the chip, and from the inlet well to the outlet well on the chip through the culture well, target cell (tumoroid) growth is promoted within the culture well.

8 Claims, 29 Drawing Sheets

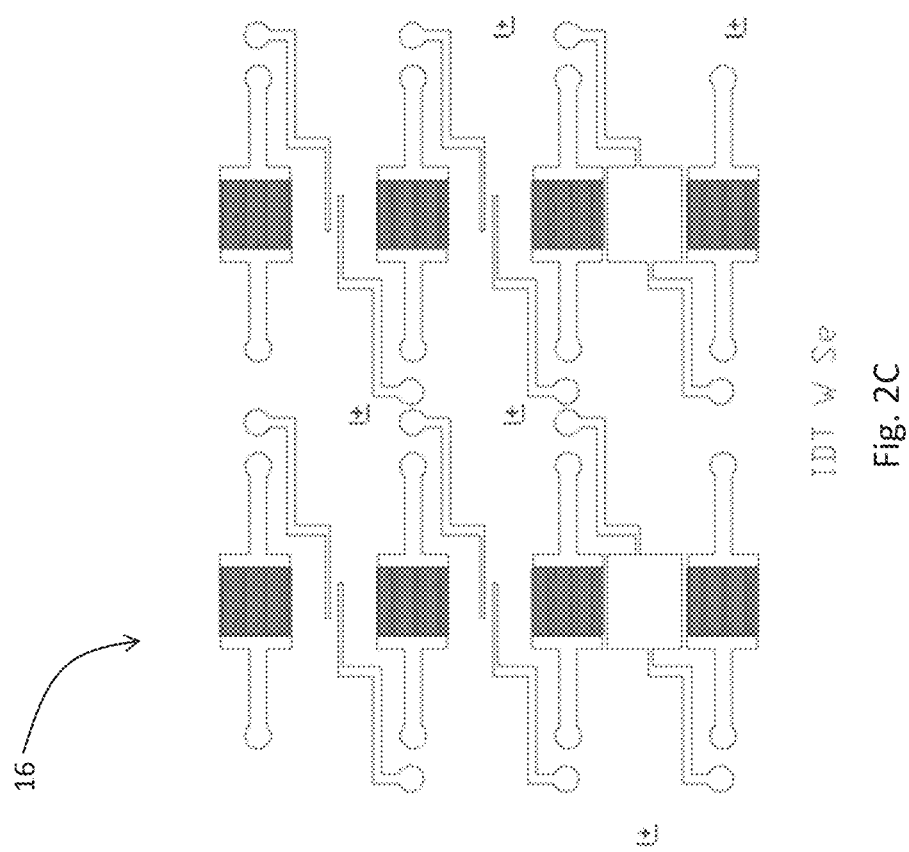

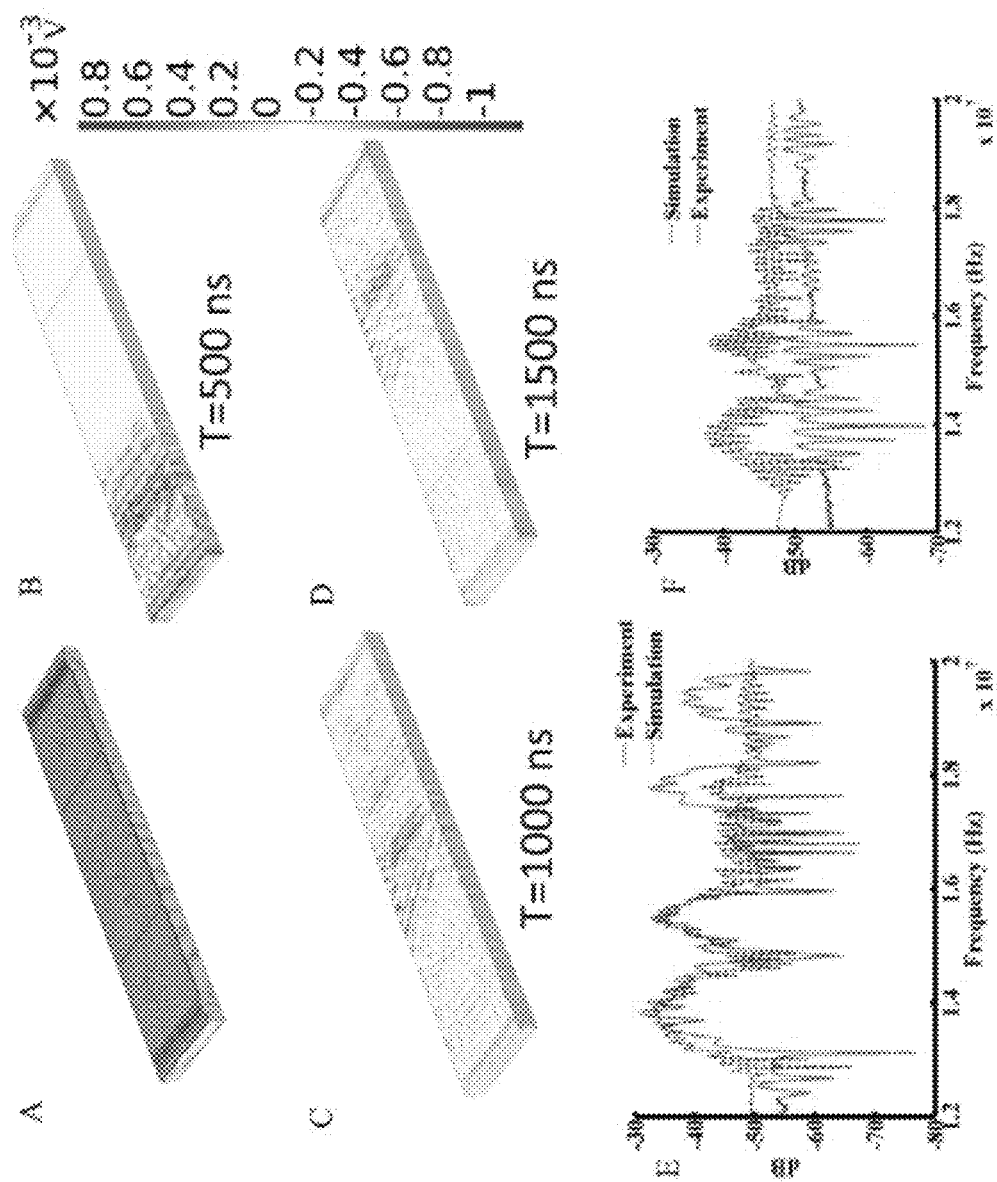
Fig. 18A-F

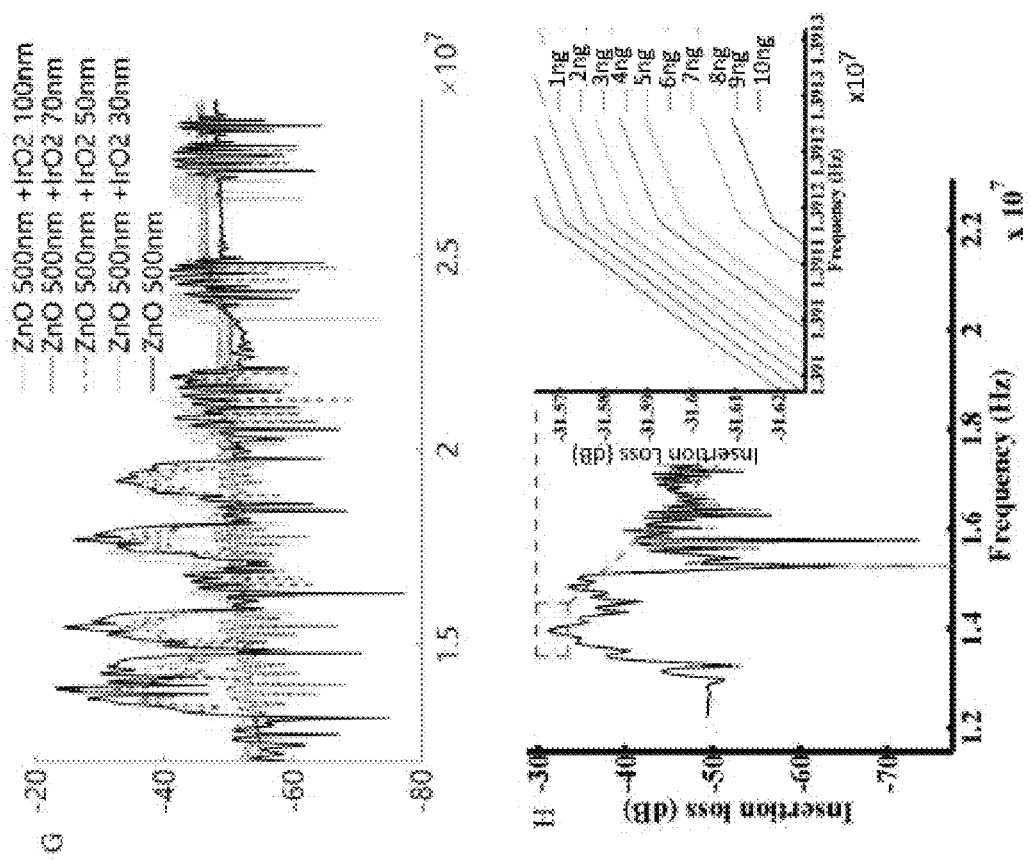
Fig. 18G-H

Table 1
Device parameters used for the simulation and fabrication of the IDT transducers.

| Parameters | Settings |
|---|---|
| Wavelength (λ) | 360 μm |
| Number of reflecting fingers | 30 pairs |
| Finger width | 75 μm |
| Wavelength of reflecting fingers | 297 μm |
| Number of fingers | 30 pairs |
| Well diameter | 6.5 mm |
| SAW velocity | 4160 m/s |
| ZnO layer thickness | 800 nm |
| MO2 layer thickness | 30 nm |
| Operation frequency | 13.991 MHz |

Fig. 22

Table 2
Comparisons to other acoustic-based pH sensors.

| Literature | Type | Top layer material | Sensitivity ($\Delta f/f$)/pH) | pH resolution |
|---|---|---|---|---|
| Qin et al. (2011) | Single layer love wave (QCM) | ZnO | $4.3 \times 10^{-4}$ | |
| Ayad et al. (2008) | | Acid copolymer layer LiTaO$_3$/ZnO | $2.0 \times 10^{-5}$ | |
| This paper | Multiple layer love wave | | $5.0 \times 10^{-5}$ | 0.011 |

4D-PERFUSED TUMOROID-ON-A-CHIP PLATFORM FOR PERSONALIZED CANCER TREATMENT APPLICATIONS

CROSS-REFERENCE TO RELATED APPLICATIONS

This nonprovisional application is a divisional of and claims priority to currently pending U.S. Nonprovisional application Ser. No. 16/799,413, entitled "4D-perfused tumoroid-on-a-chip platform for personalized cancer treatment applications," filed on Feb. 24, 2020 which is a nonprovisional of and claims priority to U.S. Provisional Application No. 62/809,305, entitled "4D-perfused tumoroid-on-a-chip platform for personalized cancer treatment applications," filed on Feb. 22, 2019, including at least one common joint inventor, the entirety of each of which is incorporated herein by reference.

FEDERALLY SPONSORED RESEARCH OR DEVELOPMENT

This invention was made with government support BX003413, IK6BX004212, IK6BX003778 by the Department of Veteran Affairs. The Government has certain rights in the invention.

BACKGROUND OF THE INVENTION

1. Field of the Invention

This invention relates, generally, to cancer treatment. More specifically, it relates to 4D-perfused tumoroid-on-a-chip platforms for personalized cancer treatment applications.

2. Brief Description of the Prior Art

Significant challenges remain in the ability to translate fundamental discoveries in cancer biology and genetics into anti-cancer drug discovery and personalized cancer therapy. Given the high failure (>90%) rate of cancer drugs, there is a need for the development of improved platforms, including 4D-perfused tumoroid-on-a-chip technologies, together with surface acoustic wave (SAW) based sensing, to improve upon the existing 2D and 3D culture systems for anticancer drug development. However, in view of the art considered as a whole at the time the present invention was made, it was not obvious to those of ordinary skill in the field of this invention how the shortcomings of the prior art could be overcome.

While certain aspects of conventional technologies have been discussed to facilitate disclosure of the invention, Applicant in no way disclaims these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for a simple and accurate is now met by a new, useful, and nonobvious invention.

The novel platform is a microfluidic device that is configured for in vitro cell growth thereon includes a microwell plate, a nanofiber disc insert on which tumor cells or tumorous are being cultured, and a surface acoustic wave sensor, together comprising a chip. The plate includes a plurality of wells each configured to receive an amount of a testing fluid therein. The disc insert is removably coupled to a bottom surface of the plate, such that the chip insert is in fluidic communication with the plurality of wells. The disc insert includes a plurality of culture wells in fluidic communication with each of an inlet well and an outlet well. A first fluid conduit is coupled to each of the inlet well and the culture well. A second fluid conduit is coupled to each of the culture well and the outlet well. Each chip set is configured to receive at least a portion of the amount of the testing fluid and circulate the testing fluid from the inlet well to outlet well via the culture well. The surface acoustic wave sensor is disposed on a bottom surface of the disc insert, with the surface acoustic wave sensor being configured to monitor a pH value associated with the disc during testing and to quantify cell growth on the chip insert. Dynamic fluid flow from the plate to the disc insert, and within the disc insert between the inlet well, culture well, and outlet well, promotes in vitro cell growth in the culture well.

In an embodiment, the first fluid conduit is oriented in a linear arrangement, such that a length of the first fluid conduit from a first end to a second end is approximately equal to a distance between the inlet well and the culture well, such that a regular fluid flow rate is achieved from the inlet well to the culture well.

In an embodiment, the second fluid conduit is arranged in an oscillating pattern, such that a length of the second fluid conduit from a first end to a second end is greater than a distance between the culture well and the outlet well, such that a reduced fluid flow rate is achieved from the culture well to the inlet well.

The inlet well, the culture well, and the outlet well may form a closed system via the first fluid conduit and the second fluid conduit, such that an equilibrium of fluid flowing through the closed system is accomplished. The fluid flowing through the system between the center well, the inlet, and the outlet may have a bidirectional flow.

A novel method of growing cells on a platform includes coupling a plate including a plurality of bottomless wells to a chip insert including a plurality of bioreactors by inserting the chip insert below the plate. As such, the plurality of bioreactors are in communication with the plurality of bottomless wells. Each of the plurality of bioreactors includes an inlet well coupled to a culture well via a first fluid conduit, and an outlet well coupled to the culture well via a second fluid conduit. An amount of a target cell to be grown on the platform is seeded on a culture fluid. The target cell may be selected from the group consisting of tumor cells, HT29, HCT116, and LLC. The seeded culture fluid is added to the plate, such that the culture fluid flows from the plate to the chip insert. 48 hours after adding the seeded culture fluid to the plate, the method includes a step of adding an additional amount of the seeded culture fluid to each of the inlet well and the culture well, with no additional seeded culture fluid added to the outlet well. As such, a volumetric difference between the inlet well and the outlet well promotes fluid flow of the seeded culture fluid into the culture well, thereby promoting cell growth of the target cell within the culture well. In an embodiment, the method includes a step of combining the chip insert with a surface acoustic wave sensor disposed beneath the chip insert, wherein the surface acoustic wave sensor quantifies cell growth of the target cell within the culture well.

A novel method of improving anticancer drug development and research includes a step of adding an amount of a target cell on a fiber inspired smart scaffold to a culture well of a microfluidic platform, with the culture well in fluidic communication with each of an inlet well and an outlet well. A first amount of a culture media is added to the inlet well, a second amount of the culture media is added to the culture well, and a third amount of the culture media is added to the outlet well. The first amount is greater than each of the second amount and the third amount; for example, in an embodiment, a difference between the first amount of the culture media and the third amount of the culture media is approximately 100 μL. The method includes a step of flowing the culture media from the inlet well toward the outlet well via the culture well due to the difference in volume between the inlet well and the outlet well. After approximately 48 hours, an amount of a testing drug is added to the fiber inspired smart scaffold. The testing drug may be selected from the group consisting of oxaliplatin, fluorouracil, and combinations thereof. An amount of the target cell remaining on the fiber inspired smart scaffold after the amount of the testing drug is added to the scaffold is then quantified.

In an embodiment, the method of improving anticancer drug development and research includes a step of coupling a plate including a plurality of bottomless wells to the microfluidic platform by inserting the microfluidic platform below the plate, such that the inlet well, the outlet well, and the culture well are in communication with the plurality of bottomless wells. An embodiment includes a step of combining the microfluidic platform with a surface acoustic wave sensor disposed beneath the microfluidic platform. In that embodiment, the step of quantifying the amount of the target cell remaining on the fiber inspired smart scaffold is performed via the surface acoustic wave sensor.

An object of the invention is to provide an improved platform for growing tumoroids on a chip, resulting in improved testing and research performance, and resulting in personalized cancer treatment applications based on the grown tumoroids.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which:

FIG. 2C depicts the SAW-based sensor layer.

FIG. 18A-F illustrates a completed mesh of the model with one pair of IDTs (interdigital transducers) and one pair of reflecting fingers at both input and output port in section A. Sections B, C, and D are the surface acoustic wave electrical perturbation at the surface of Lithium Tantalate. Section E illustrates a comparison between simulation and experiment frequency response for the device (with 100 nm Cr IDTs+500 nm ZnO+30 nm $IrO_2$) from 12 MHz to 20 MHz. Section F illustrates a comparison between simulation and experiment frequency response for the device (with 100 nm Cr IDTs+500 nm ZnO+70 nm $IrO_2$) from 12 MHz to 20 MHz.

FIG. 18G-H are a series of graphs. Section G illustrates the frequency spectrum of different $IrO_2$ coating layers on the device measured by the network analysis. Increasing the $IrO_2$ layer on the top of the device decreases the Insertion loss. After depositing ~100 nm $IrO_2$ on the surface, the acoustic wave ceased propagating at the surface by the conductive IrO2 layer. Section H illustrates the device model response to different mass loading changes of the $IrO_2$ layer.

FIG. 22 is a table including device parameters used for the simulation and fabrication of the IDT transducers.

FIG. 23 is a table comparing the SAW based sensors to prior art acoustic-based pH sensors.

DETAILED DESCRIPTION OF THE INVENTION

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

As used in this specification and the appended claims, the singular forms "a," "an," and "the" include plural referents unless the content clearly dictates otherwise. As used in this specification and the appended claims, the term "or" is generally employed in its sense including "and/or" unless the context clearly dictates otherwise.

Figure 1:
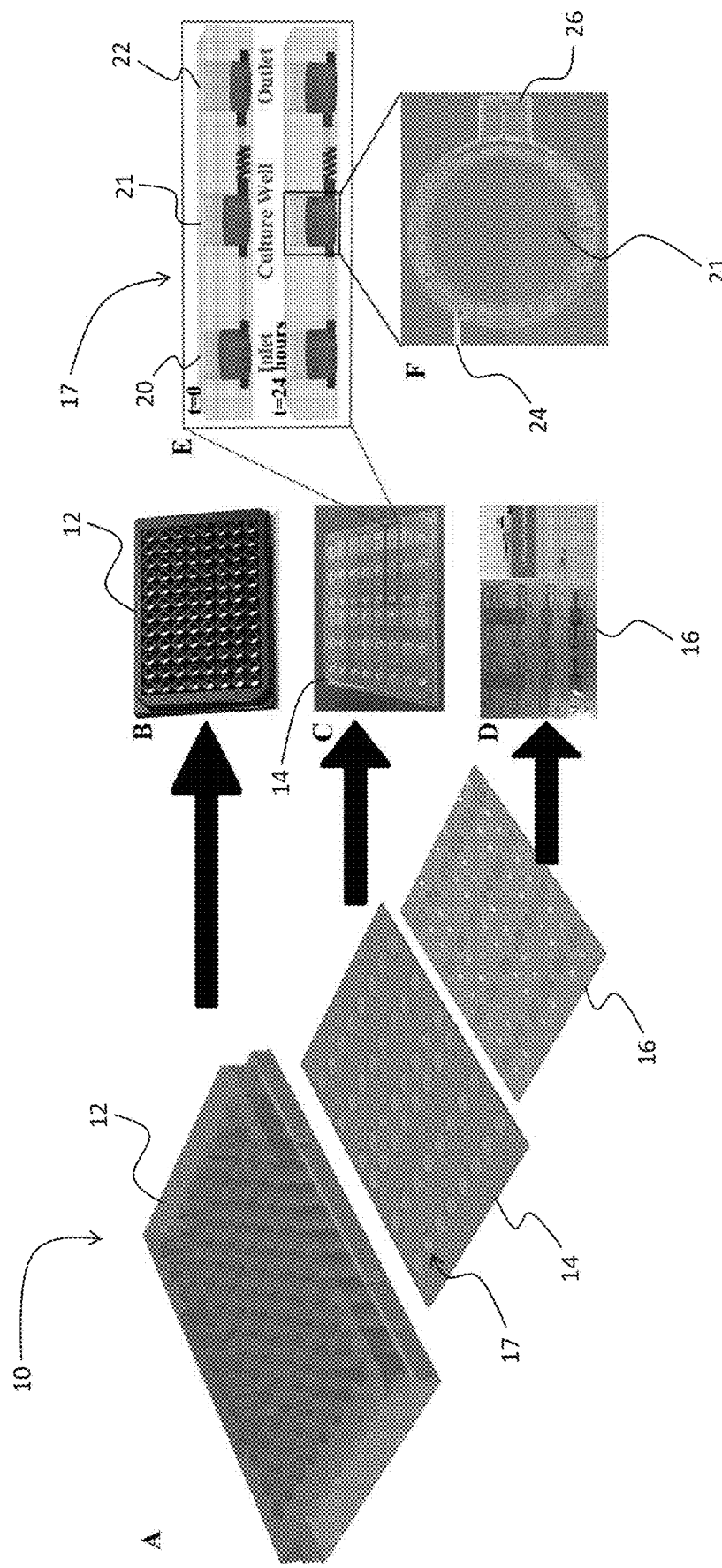
FIG. 1 depicts an embodiment of a 4D-perfusable tumoroid-on-a-chip platform, in accordance with an embodiment of the present invention. Section A of FIG. 1 depicts the platform in a disassembled configuration. Section B of FIG. 1 depicts a bottomless well plate component of the platform, including 96 wells; section C of FIG. 1 depicts a microfluidic channel layer of the platform that resides below the bottomless well plate; and section D of FIG. 1 depicts a surface acoustic wave (SAW) based sensor layer of the platform that resides below the microfluidic channel layer. Section E is a close-up view of an individual chip, or bioreactor, on the microfluidic channel layer of the platform, and section F is a close-up view from a top-down perspective of a culture well of a chip of section E.
Figure 2A:
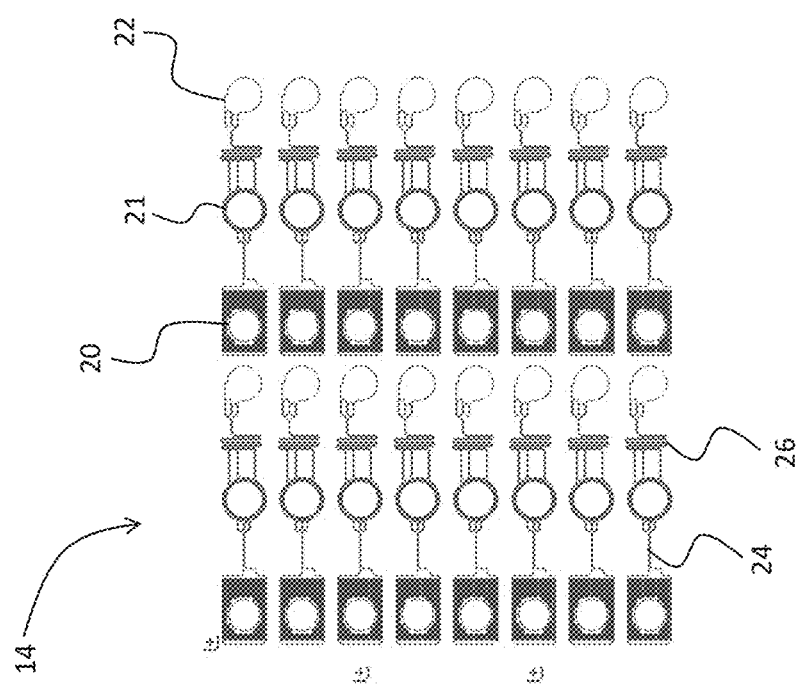
FIG. 2A depicts the microfluidic channel layer prior to integration with the SAW-based sensor layer.
Figure 2B:
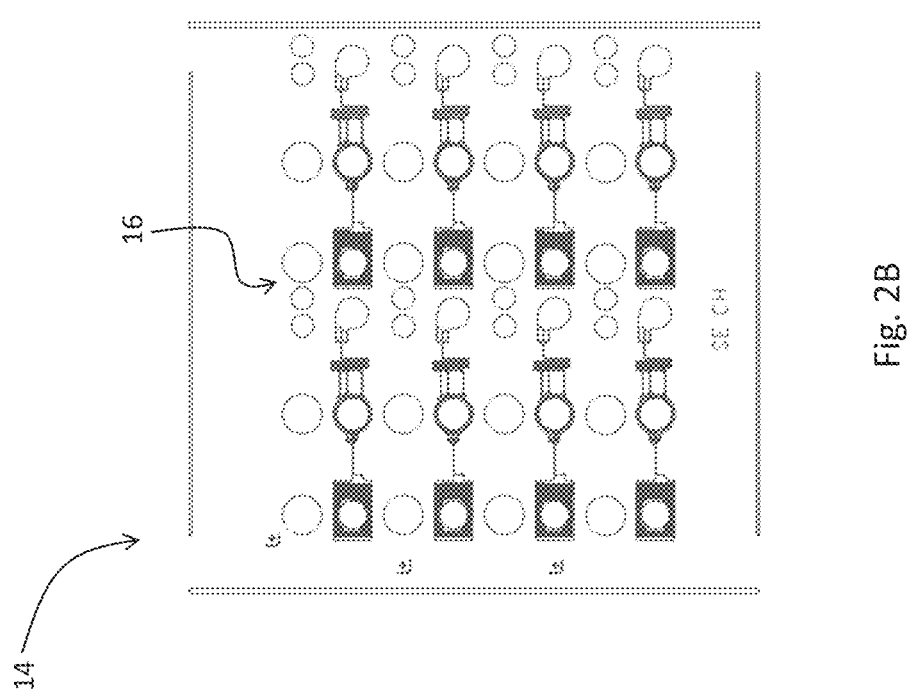
FIG. 2B depicts the microfluidic channel layer integrated with the SAW-based sensor layer.

The present invention includes a 4D-perfused tumoroid-on-a-chip platform that can be used in personalized cancer treatment. As shown in FIG. 1, the platform 10 includes a plate 12 with a plurality of bottomless wells that resides atop a microfluidic channel layer 14, which in turn resides atop a surface acoustic wave (SAW) based sensor layer 16 that is capable of measuring potential pH values of fluids disposed within the platform. The microfluidic channel layer 14 includes a plurality of bioreactors 17, with each bioreactor 17 including an inlet well 20, a culture well 21, and an outlet well 22. The inlet well 20, culture well 21, and outlet well 22 form a closed system via fluid conduits 24, 26 spanning from the inlet well 20 to the culture well 21, as well as from the culture well 21 to the outlet well 22. FIGS. 2A-2C depict microfluidic channel layer 14 and SAW-based sensor layer 16 in greater detail, showing the fluid flow relationship between inlet well 20, culture well 21, and outlet well 22.

Figure 3B:
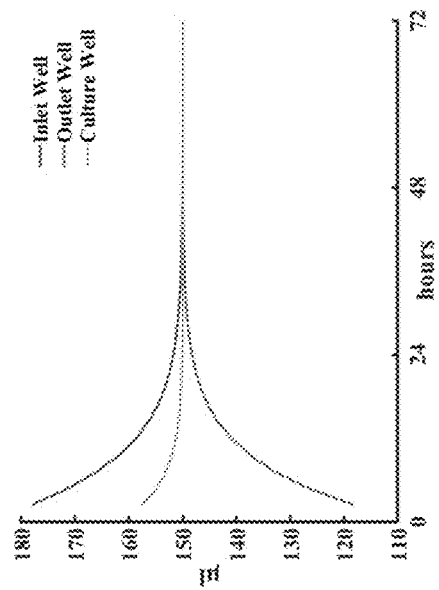
FIG. 3B is a graphical representation of flow rate over time, comparing the inlet well, the culture well, and the outlet well of an individual bioreactor of the microfluidic channel layer of the platform.
Figure 3A:
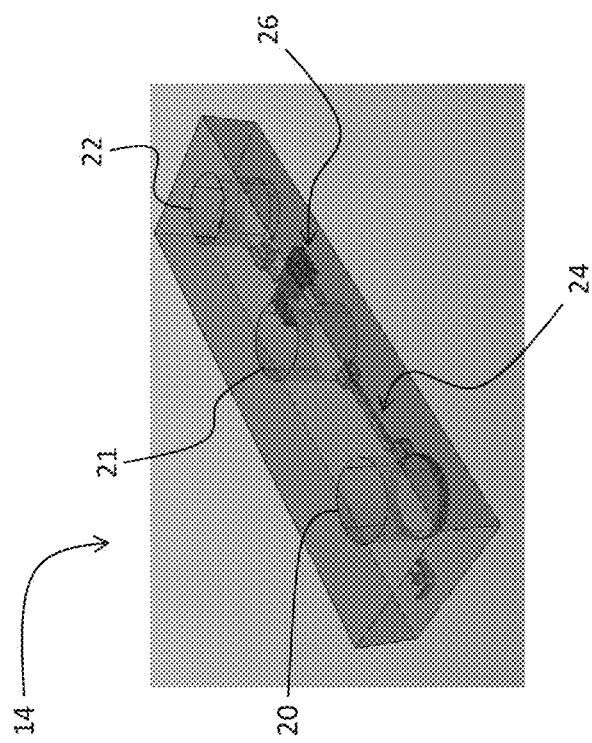
FIG. 3A depicts the microfluidic channel layer in a perspective view.

FIG. 3A in particular depicts an embodiment of microfluidic channel layer 14 of platform 10. Residing below plate 12 including the plurality of bottomless wells, microfluidic channel layer 14 received fluid disposed within the wells of plate 12. The fluid received by microfluidic channel layer 14 circulates between inlet well 20, culture well 21, and outlet well 22, such that a closed relationship is formed between the wells via fluid flow therebetween. Accordingly, inlet well 20 is fluidically coupled to culture well 21 via at least one fluid conduit 24 and culture well 21 is fluidically coupled to outlet well 22 via at least one fluid conduit 26. FIG. 3B graphically depicts the equilibrium achieved over time due to the fluid flow between inlet well 20, culture well 21, and outlet well 22. The fluid dynamic equations used to calculate flow within the system is as follows:

$$\frac{dV_s}{dt} = \frac{V_{cc} - V_s}{\tau_{s-cc}} \quad (1)$$

$$\frac{dV_{cc}}{dt} = \frac{V_s - V_{cc}}{\tau_{s-cc}} + \frac{V_w - V_{cc}}{\tau_{cc-w}} \quad (2)$$

$$\frac{dV_w}{dt} = \frac{V_{cc} - V_w}{\tau_{cc-w}} \quad (3)$$

To control the flow of fluid within the system, the at least one fluid conduit 24 between inlet well 20 and culture well 21 is sized and shaped such that a regular flow rate can be achieved between inlet well 20 and culture well 21. For example, as depicted in FIG. 3A, the at least one fluid conduit 24 is a substantially linear and uniform conduit directly connecting inlet well 20 and culture well 21, such that a length of the at least one fluid conduit 24 is substantially equal to a distance between inlet well 20 and culture well 21. To further control the flow of fluid within the system, the at least one fluid conduit 26 between culture well 21 and outlet well 22 is sized and shaped such that a reduced flow rate can be achieved between culture well 21 and outlet well 22. For example, as depicted in FIG. 3A, the at least one fluid conduit 26 is arranged in an oscillating pattern. Said another way, the at least one fluid conduit 26 has a length that is much greater than a lateral distance separating a first end of the conduit from a second end of the conduit. As such, the at least one fluid conduit 26 is arranged such that the conduit coils along a horizontal axis in an oscillating pattern between the first end and the second end. As a result, the body of the at least one fluid conduit 26 includes substantially equally sized portions that are adjacent to each other between opposing ends of the conduit. In another embodiment, the at least one fluid conduit 26 is arranged as a coiled pipe that coils along a vertical axis, such that body portions of the conduit oscillate between an upper position and a lower position with respect to a connection point to each of culture well 21 and outlet well 22.

Figure 4C:
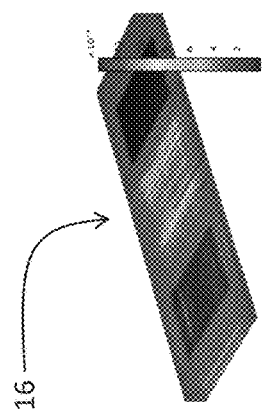
FIG. 4C is a finite element analysis optimization of the SAW measuring wave displacement.
Figure 4B:
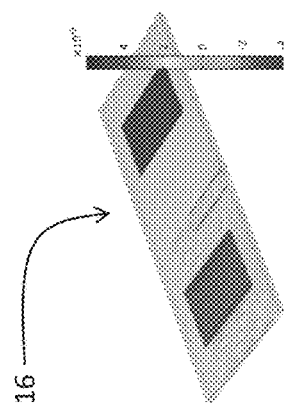
FIG. 4B is a finite element analysis optimization of the SAW measuring potential distribution.
Figure 4A:
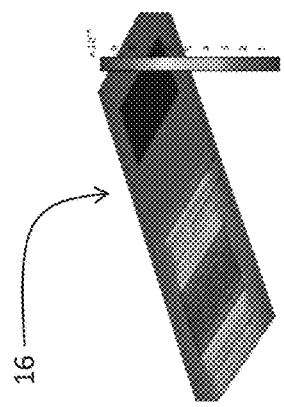
FIG. 4A is a finite element analysis optimization of the SAW measuring wave propagation.
Figure 4D:
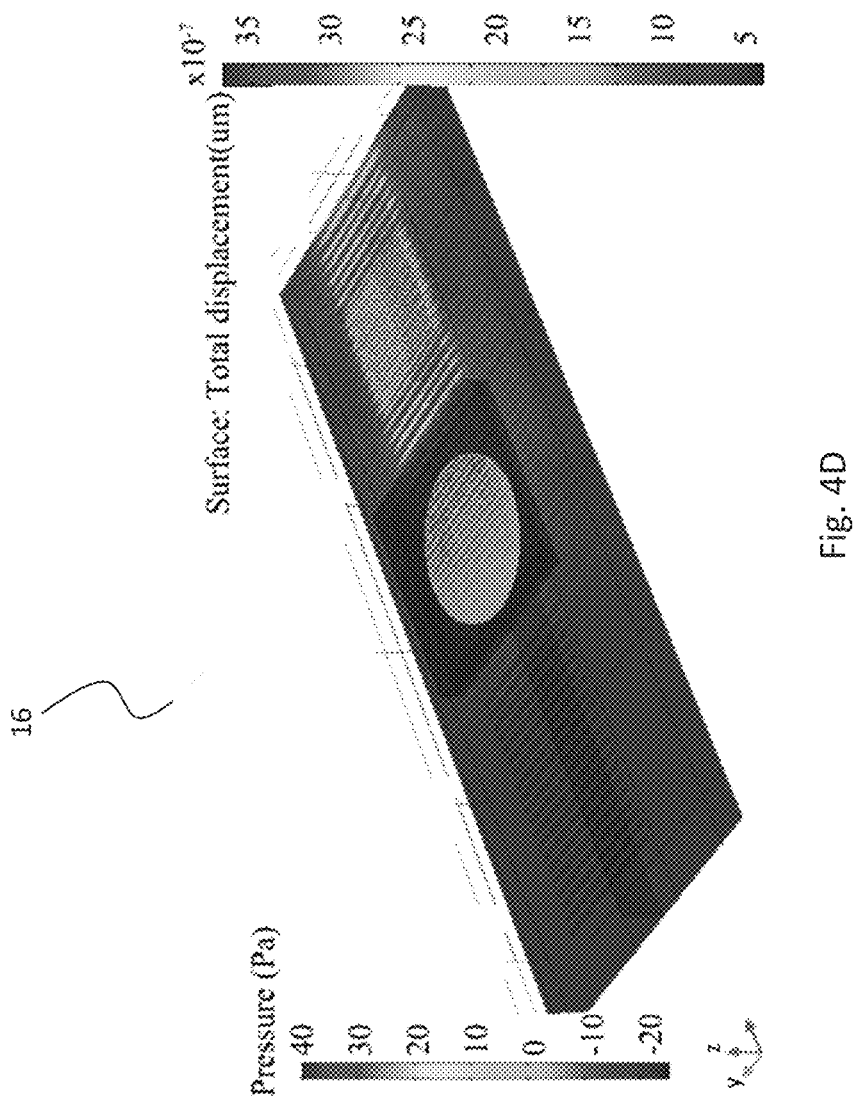
FIG. 4D is a finite element analysis optimization of the SAW measuring pressure generated on the culture medium due to the waves traveling into the liquid.

FIGS. 4A-4D depict various finite element analysis optimization measurements taken on SAW-based sensor layer 16. SAW-based sensor layer 16 is integrated with microfluidic channel layer 14, residing below microfluidic channel layer 14 on the assembled platform 10. A full optimization of sensor 16 settings and flow rate was conducted by finite element analysis to increase the sensitivity and generate appropriate shear stress on cells. For example, as shown in FIGS. 4A-4C, SAW wave propagation simulations (FIG. 4A) provide ways to study the potential distribution (FIG. 4B) and wave displacement (FIG. 4C) on the lithium tantalite ($LiTaO_3$) SAW. Moreover, as shown in FIG. 4D, finite element analysis the wave travelling into the liquid culture medium can study the pressure generated on the culture medium.

Figure 5A:
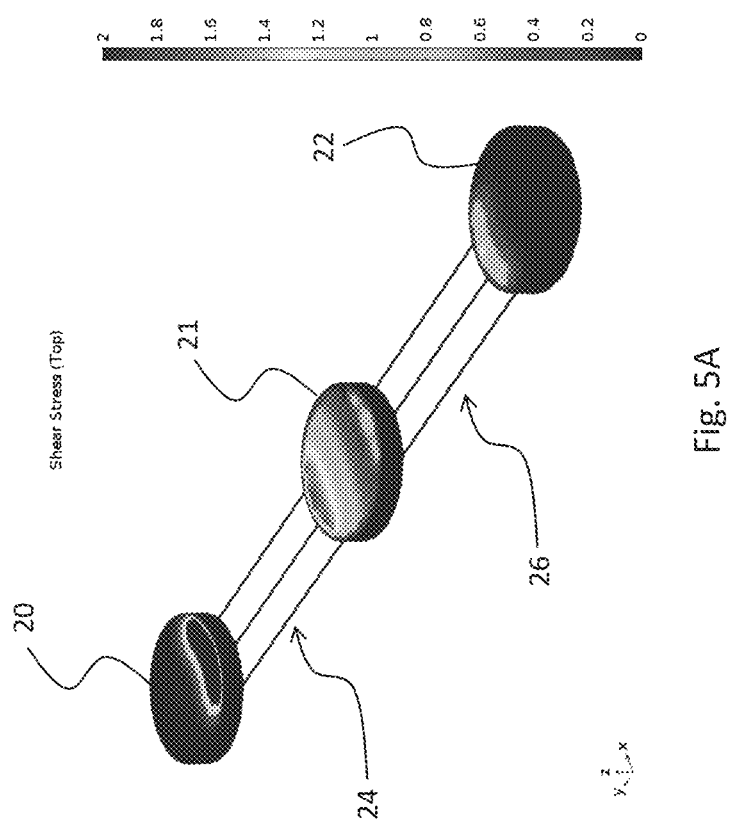
FIG. 5A is a finite element analysis depicting shear stress on the top side of the inlet well, the culture well, and the outlet well of an individual bioreactor of the microfluidic channel layer of the platform.
Figure 5B:
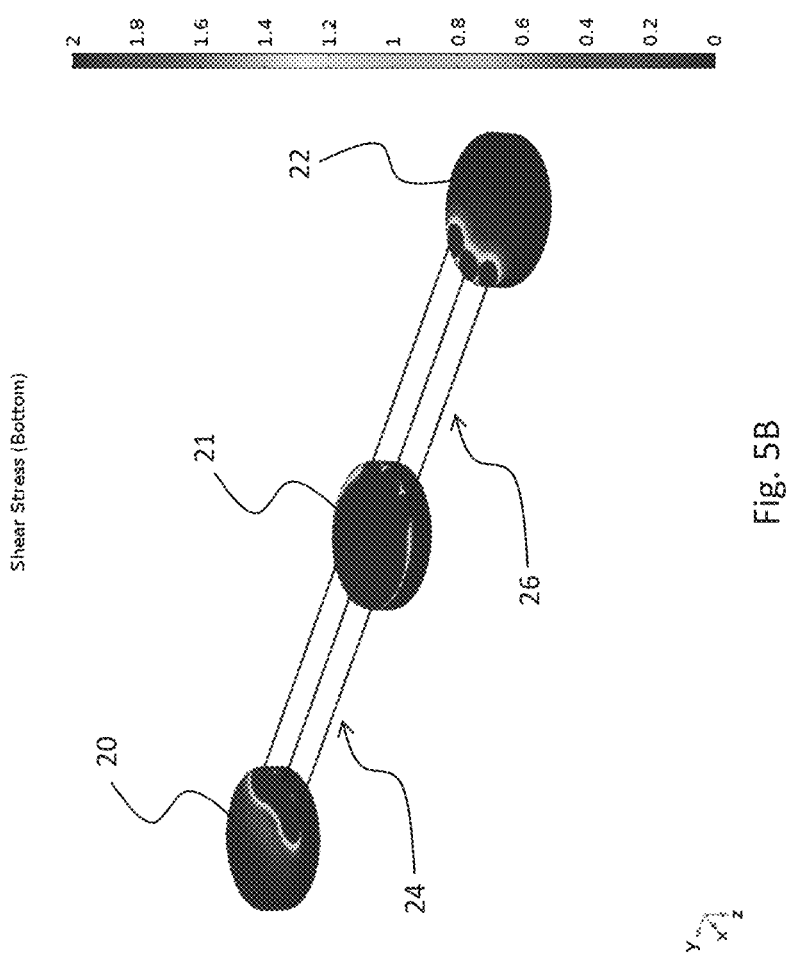
FIG. 5B is a finite element analysis depicting shear stress on the bottom side of the inlet well, the culture well, and the outlet well of an individual bioreactor of the microfluidic channel layer of the platform.

In addition, FIGS. 5A-5B depict the results of finite element analysis calculations performed on inlet well 20, culture well 21, and outlet well 22 to measure the shear stress experienced by the top surface and bottom surface of each well. As shown in FIGS. 5A-5B, the bottom surface of culture well 21 experiences the greatest degree of shear stress across the entirety of culture well 21. In addition, the top surface of culture well 21 experiences shear stress across its entirety. Both the top surface and the bottom surface of inlet well 20 experiences a greater degree of shear stress on a side proximate to culture well 21. The top surface of outlet well 22 experiences minimal shear stress that is concentrated on a side proximate to culture well 21, with a greater degree of shear stress experienced on the bottom surface of outlet 22 proximate to culture well 21.

Methods of Manufacture

Platform 10 is manufactured by a traditional MEMS (microelectromechanical systems) fabrication. PDMS (polydimethylsiloxane) molds of plate 12 were fabricated by the traditional micro-lithography methods, while microfluidic channel layer 14 was fabricated by the conventional PDMS micro molding technique. The microfluidic channel layer 14 molds are fabricated by using soft lithography on a 5-inch SU-8 silicon mold. The PDMS layer is then replicated from the customized SU-8 master mold and 3 mm holes are punched for inlet wells 20, culture wells 21, and outlet wells 22.

After the micro-molding process, the platform is assembled in two steps. The PDMS layer (subjected to a 75° C. oven for two hours with a PMMA, or Poly(methyl methacrylate), sandwich, and then placed for 20 minutes in 4° C. refrigerator) is first attached to a 3×4 inch glass slide. The bottom of plate 12 is bonded to microfluidic channel layer 14 by a chemical gluing method. Briefly, the polystyrene plastic bottom (96-Well No-Bottom Plates, Greiner Bio-One) of plate 12 is immersed into a 4% (v/v) aqueous solution of 3mercaptopropyl trimethoxysilane (Sigma-Aldrich) diluted in 98% methanol, for 2 hours. After hydrolysis and nucleophilic reactions, the alkoxysilane-terminated substrate on the plastic bottom of plate 12 is rinsed with distilled water and dried with Argon.

The glass slide is bonded to the bottom of the PDMS layer by treating with oxygen plasma for 2 minutes 30 seconds. The surface-modified well plate 12 and the PDMS layer with the glass slide are then treated with oxygen plasma for 2 minutes, aligned, and bonded together. The fully assembled platform 10 is subjected to a temperature of 50° C. for two hours, covered with a standard 96-well plate polystyrene lid. Before cell cultures are added, the assembled platform 10 was exposed to oxygen plasma for 12 minutes followed with sterilization using 75% ethanol, and finally subjected to UV light for 1-hour just prior to use.

Experimental Results

Figure 6:
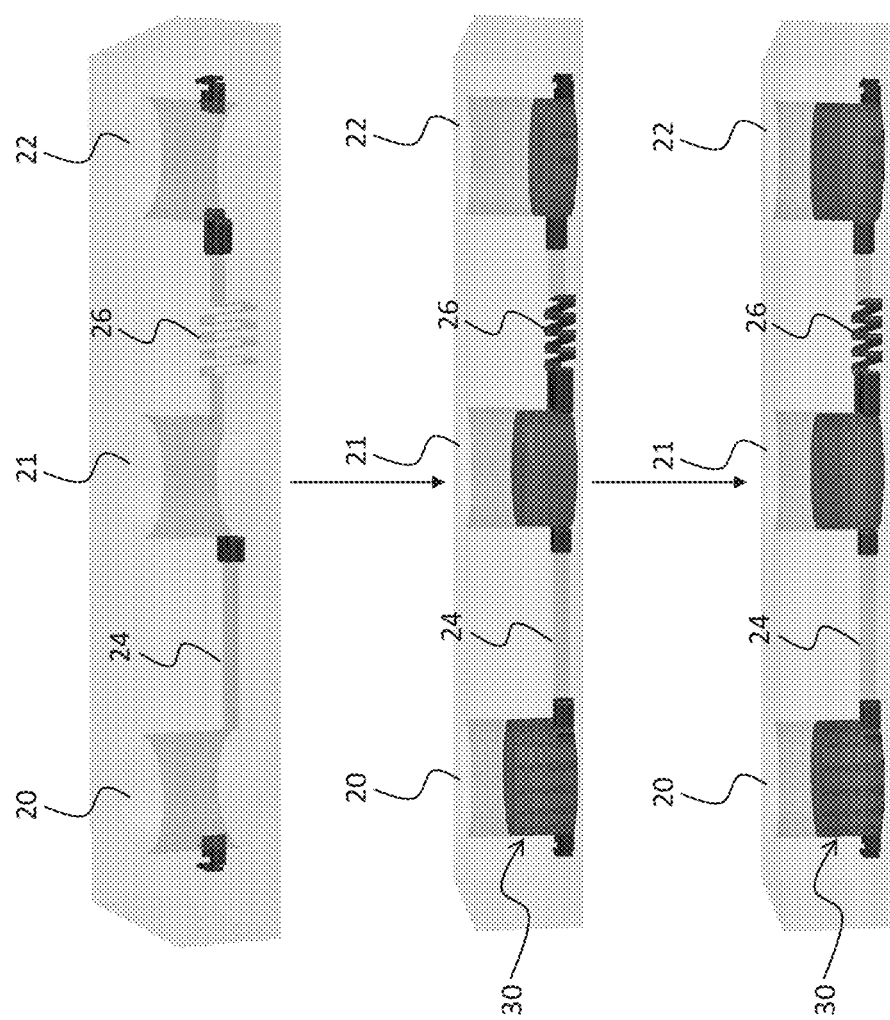
FIG. 6 depicts experimental results of fluid flow over time through an individual bioreactor of the microfluidic channel layer of the platform.

FIG. 6 depicts the results of experiments performed on platform 10 described in detail above. In a first step, microfluidic channel layer 14 is cleaned and a scaffold to be grown on platform 10 is washed. Either 3000 cells of HT29, 2000 cells of HCT116, of 3500 cells of LLC are seeded in 100 µL of a culture media 30. After 48 hours, an additional 100 µl of the culture media 30 is added to inlet well 20, and an additional 50 µL of the culture media is added to culture well 21, with no fresh media added to outlet well 22. Approximately 48 hours after the additional media is added, a drug response test is performed. All the culture media 30 is removed from culture well 21, and 300 µL of a drug dissolved media is added to culture well 21 at the control plate. An additional 250 µL of the drug dissolved media is added to inlet well 20; an additional 200 µL of the drug dissolved media is added to culture well 21; and an additional 150 μL of the drug dissolved media is added to outlet well 22. The fluid flows between the wells due to the difference in initial fluid volumes between inlet well 20, culture well 21, and outlet well 22.

A test, such as a CELLTITER-GLO® test, is performed 48 hours later to quantify the viable cells in the culture. To perform the test, cells were treated with varying concentrations of a drug (such as Oxaliplatin, Fluorouracil, and combinations thereof) for 48 hours in a regular 96 well plate (such as plate 12 with a plurality of bottomless wells) with a Fiber inspired smart scaffold (FiSS) disposed on a microfluidic 96 well plate with FiSS cultures (microfluidic channel layer 14). Drugs were added on day 5 of the growth of the FiSS culture. Cell viability was determined using a CELLTITER-GLO® assay (Promega) according to the manufacturer's protocol. Luminescence was measured in a white well-plate in a Bio-Tek Synergy H4 plate reader (BioTek). An average luminescence value for each group was plotted as a percentage of the control group. A non-linear regression was then run to calculate the IC50 (half maximal inhibitory concentration) value. Drugs were obtained from LC Laboratories and Sigma Aldrich. 2% Lipogro Bovine Cholesterol Concentrate was purchased from Rocky Mountain Biologicals, Inc.

Figure 7:
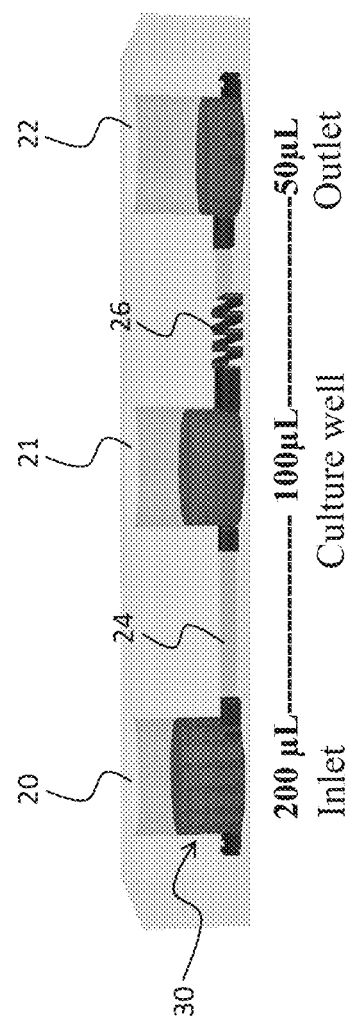
FIG. 7 depicts an experimental culture well including 200 μL of fluid in the inlet well, 100 μL of fluid in the culture well, and 50 μL of fluid in the outlet well.
Figure 8B:
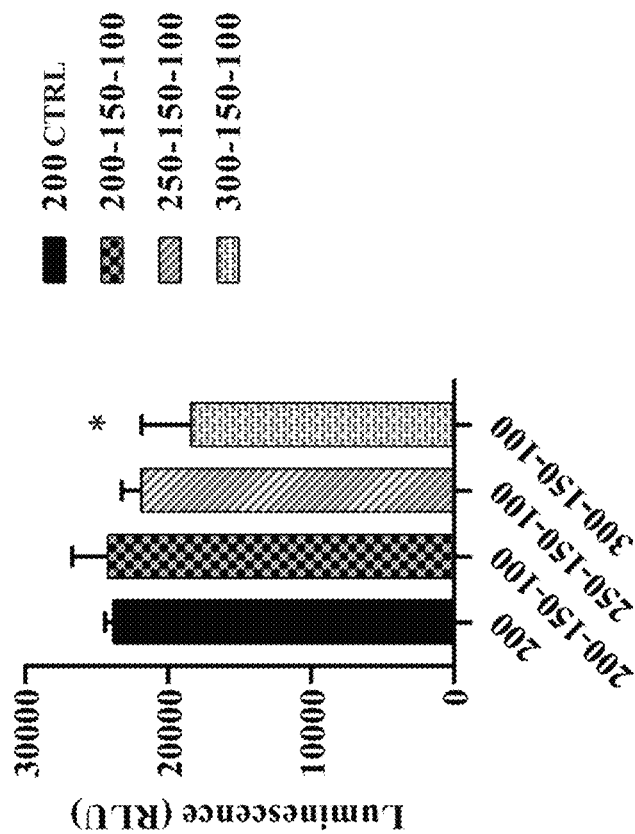
FIG. 8B is a graphical representation of luminescence (measured in RLU) comparing culture well including an equal amount of fluid (labelled as 200 CTRL) with wells including different amount of fluid (labelled as 200-150-100, 250-150-100, and 300-150-100, respectively).
Figure 8A:
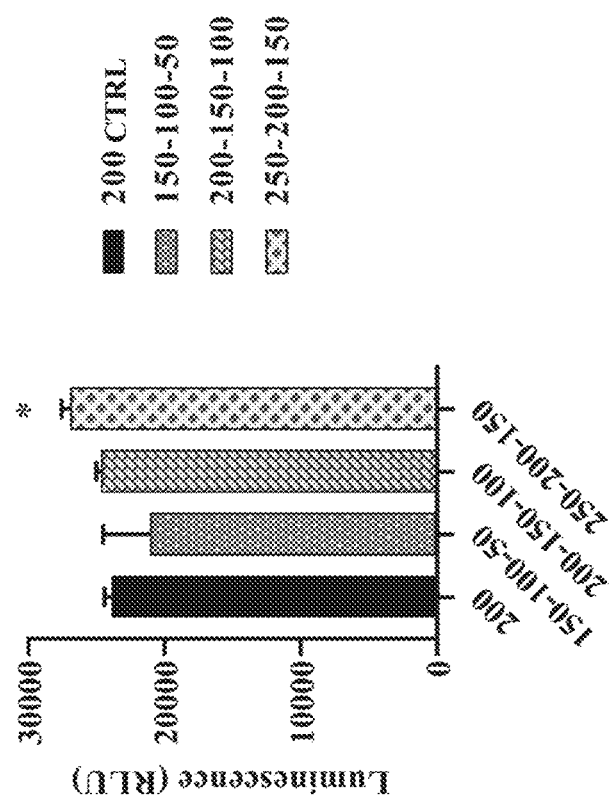
FIG. 8A is a graphical representation of luminescence (measured in RLU) comparing culture well including an equal amount of fluid (labelled as 200 CTRL) with wells including different amount of fluid (labelled as 150-100-50, 200-150-100, and 250-200-150, respectively).

An exemplary test setup is shown in FIG. 7, with testing results depicted in FIGS. 8A-8B. The results depicted in FIG. 8A indicate that a fixed volume difference of media 30 between inlet well 20 and outlet well 22 (100 μL of a difference), the flow rate and shear stress will be the same. The viability of HT29 cells grow in the device shows the similar results compared to the control group in the regular 96 plate. FIG. 8B depicts results indicating that an increase in the difference between the volume of the media 30 between inlet well 20 and outlet well 22 (i.e., 100 μL of a difference, 150 μL of a difference, and 200 μL of a difference) the flow rate and shear stress will be increased. FIG. 8B shows that the viability of HT-29 cells grown in the device decreased as the shear stress increased. The asterisk (*) in FIGS. 8A-8B indicates a p-value of $<(0.05)$.

Figure 9A:
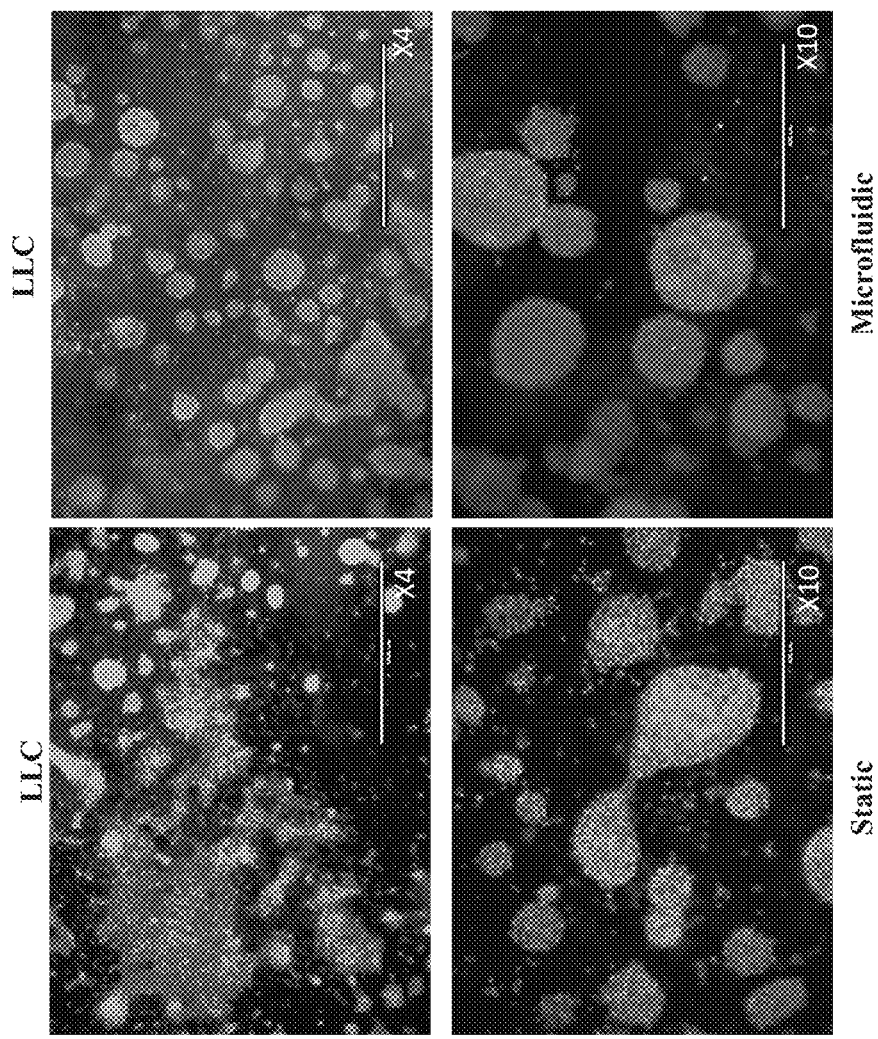
FIG. 9A depicts tumoroid morphology for Lewis lung carcinoma (LLC) cells comparing static systems with microfluidic systems.
Figure 9B:
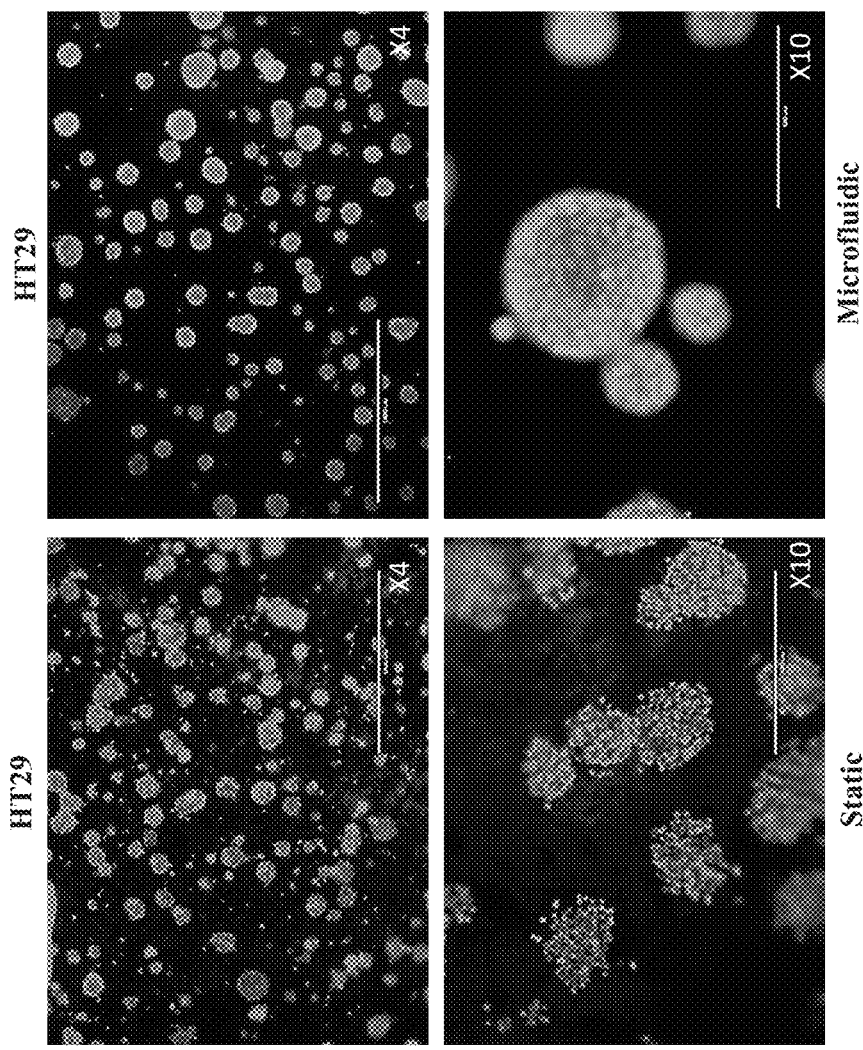
FIG. 9B depicts tumoroid morphology for HT29 cells comparing static systems with microfluidic systems.
Figure 10:
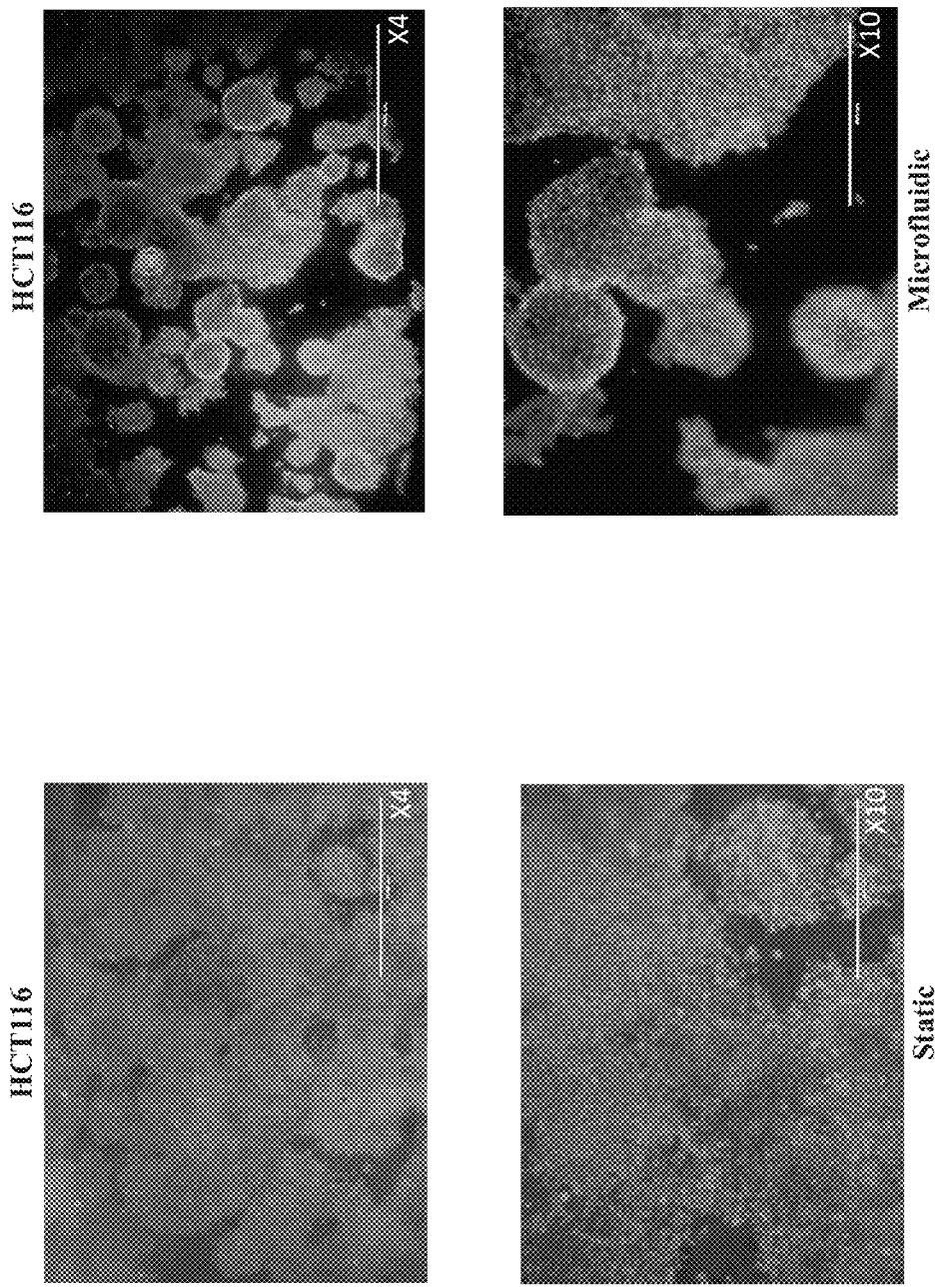
FIG. 10 depicts tumoroid morphology for HCT116 cells comparing static systems with microfluidic systems.
Figure 11:
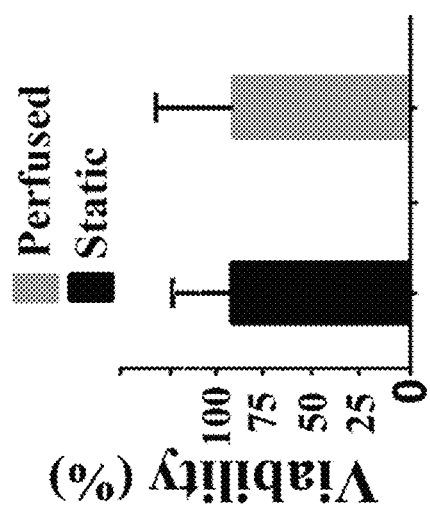
FIG. 11 is a graphical representation of chip biocompatibility comparing perfused (microfluidic) and static systems for HT29 cells, showing no statistical difference between the systems.

Platform 10 shows improved tumoroid growth results as compared with static, non-microfluidic systems, and shown in FIGS. 9A-9B and 10. FIG. 9A depicts comparisons of LLC cell growth on a static (control) platform versus LLC cell growth on microfluidic platform 10, showing improved growth on platform 10. Similarly, FIG. 9B depicts comparisons of HT29 cell growth on a static (control) platform versus HT29 cell growth on microfluidic platform 10, showing improved growth on platform 10, and FIG. 10 depicts comparisons of HCT116 cell growth on a static (control) platform versus HCT116 cell growth on microfluidic platform 10, showing improved growth on platform 10. As a baseline test, FIG. 11 depicts that platform 10 performs at least as well as a static system for the viability of HT29 cells.

Figure 12B:
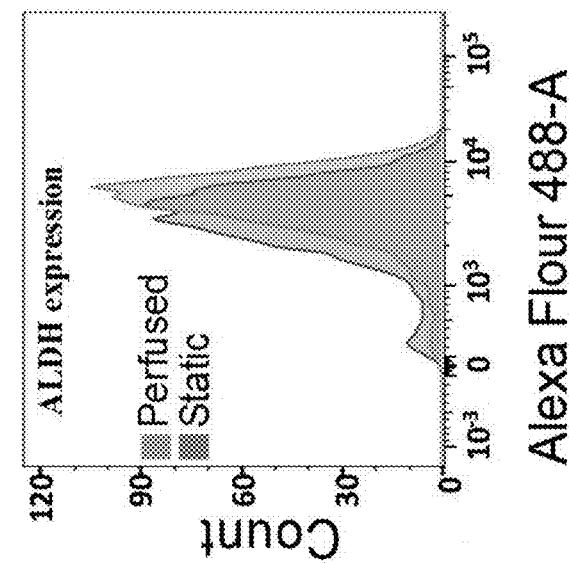
FIG. 12B is a graphical representation of aldehyde dehydrogenase (ALDH) expression comparing a static culture with a microfluidic/perfused culture in colon cancer cell lines.
Figure 12A:
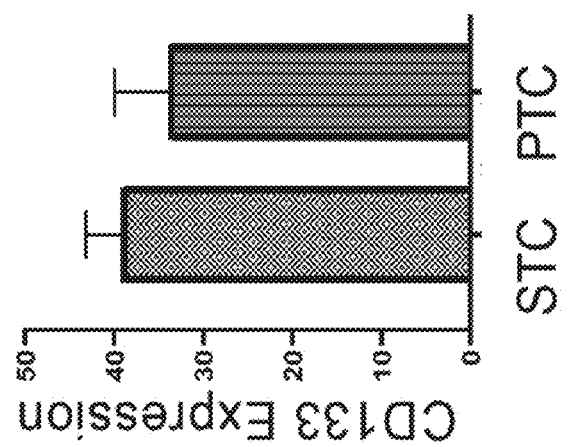
FIG. 12A is a graphical representation of CD133 expression comparing a static culture (STC) with a microfluidic/perfused culture (PTC).

In addition, FIGS. 12A-12B graphically depict the comparison between static (STC) and platform 10 (PTC) based systems, specifically comparing the expression of the CD113 gene with HT29 cells used on the testing platform. Platform 10 was found to have a decreased CD113 expression as compared with static, prior art platforms. FIG. 12B depicts a differential expression flow cytometry histogram of ALDH comparing static systems with platform 10 for colon cancer cell lines. Platform 10 experienced increased ALDH expression as compared with prior art, static platforms.

Figure 13:
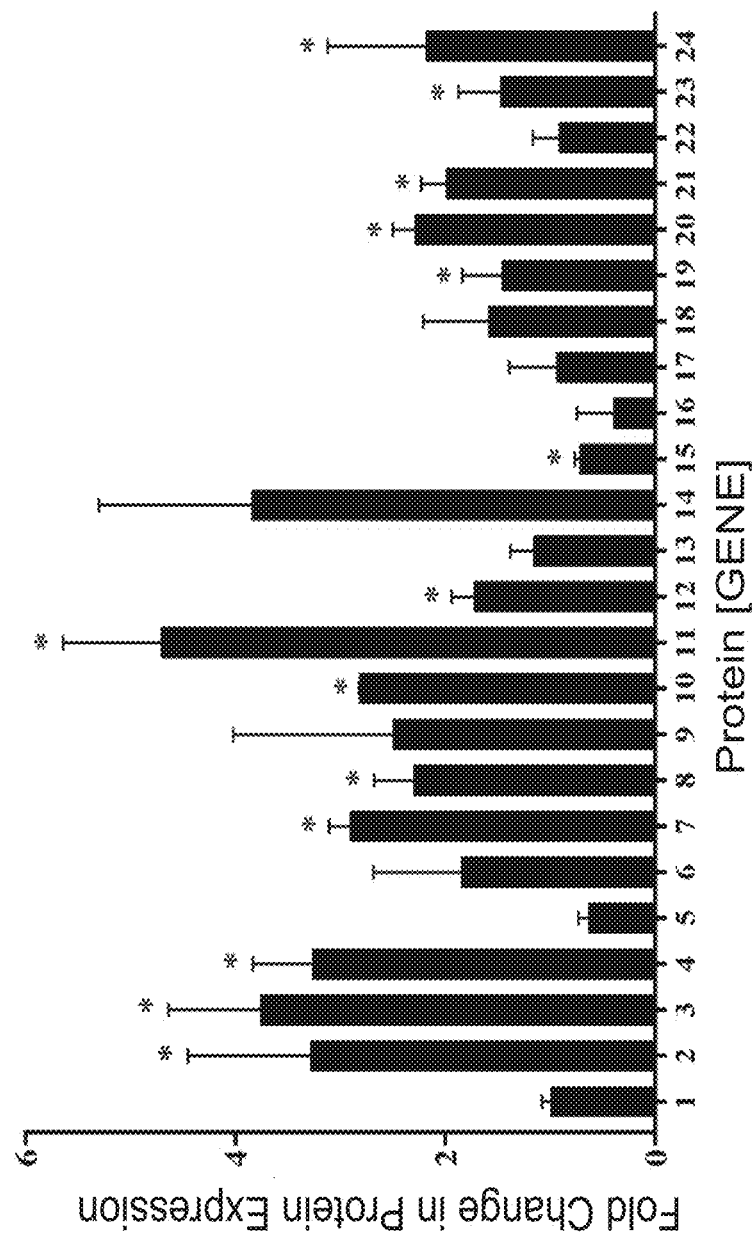
FIG. 13 is a graphical representation of changes in protein expression for HT29 cells under microfluidic systems, in accordance with an embodiment of the present invention.

FIG. 13 depicts the difference in tumoroid culture protein expression for platform 10 as compared with static platforms and cultures. The numbers along the x-axis of the graph depicted in FIG. 13 correspond to the following proteins: 1. Control, 2. CEA, 3. VEGF-A, 4. CRP, 5. NSE, 6. DKK1, 7. YNFRSF11B, 8. PAI-1, 9. PSA-free, 10. Galectin-3, 11. RANTES, 12. GDF-15, 13. β-2 Micro, 14. HGF, 15. TGF-β1, 16. bFGF, 17. Thrombospondin 1, 18. Ca125, 19. MMP2, 20. IL-8, 21. TIMP1, 22. CA19-9, 23. MIF, 24. uPA. CEA, Galectin-3, and MMP2 are tumor antigens; CRP, RANTES, and IL-8 are cancer inflammation proteins; VEGF-A and uPA are angiogenesis proteins; and YNFRSF11B, TIMP1, MIF, and TGF-β1 are tumorigenicity regulation proteins. FIG. 13 shows increased secretomes for platform 10 as compared with static systems using cancer discovery arrays. The secreted proteins in supernatants were subjected to a QUANTIBODY® array test to compare expressions in platform 10 vs static systems. The ratio of expression in platform 10 to static systems is expressed as fold changes along the y-axis of the graph depicted in FIG. 13. The data is an average of triplicates and a Student t-test was used for significance (*=P<0.05).

Figure 14C:
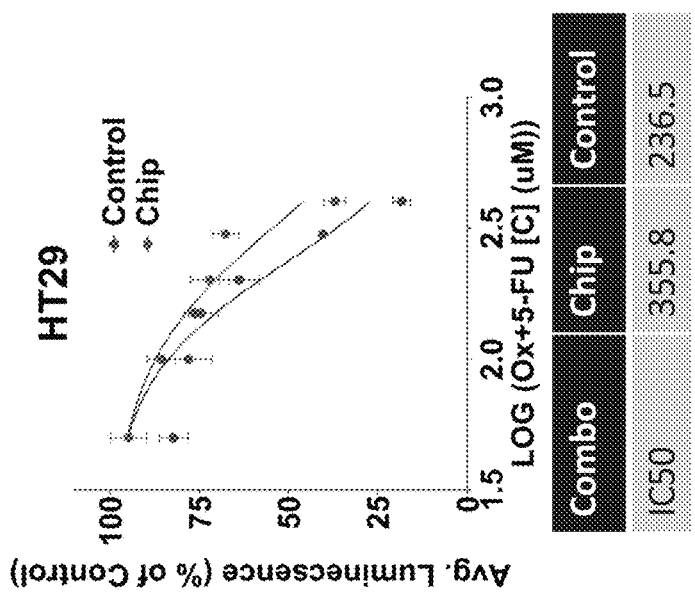
FIG. 14C is a graphical representation depicting the drug response of HT29 cells, comparing a control system compared with the microfluidic systems described herein.
Figure 14B:
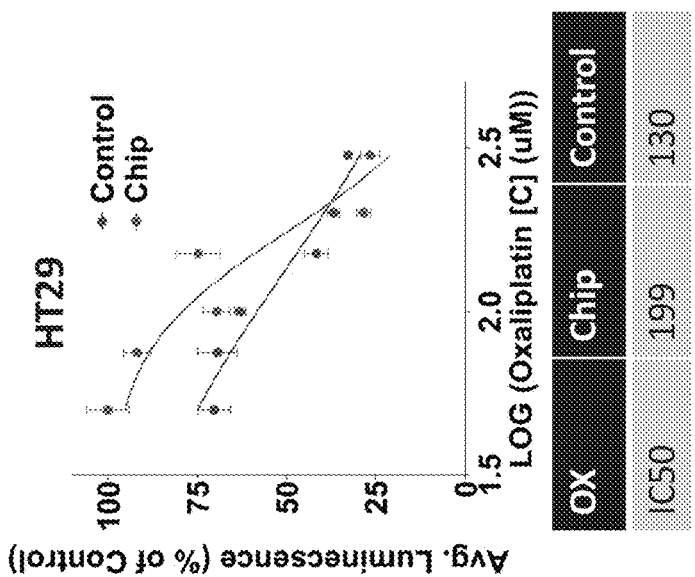
FIG. 14B is a graphical representation depicting the drug response of HT29 cells, comparing a control system compared with the microfluidic systems described herein.
Figure 14A:
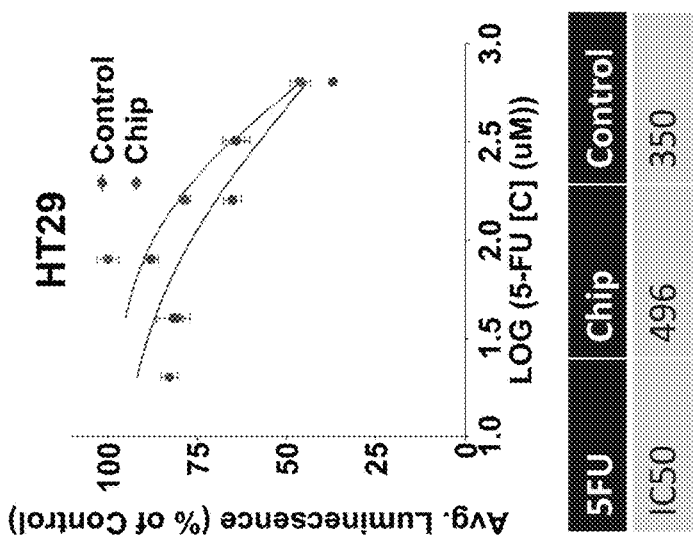
FIG. 14A is a graphical representation depicting the drug response of HT29 cells, comparing a control system compared with the microfluidic systems described herein.

FIGS. 14A-14C depict the drug response of platform 10 (labeled as Chip) compared with a static system (labeled as Control) for HT29 tumoroid cells. The drug used in FIG. 14A is fluorouracil (5FU); the drug used in FIG. 14B is oxaliplatin (OX); and the drug used in FIG. 14C is a combination of oxaliplatin and fluorouracil in a 1:2.5 ratio. For each of the tests, platform 10 requires a higher drug dose to have the same IC50 as the static systems.

Figure 15C:
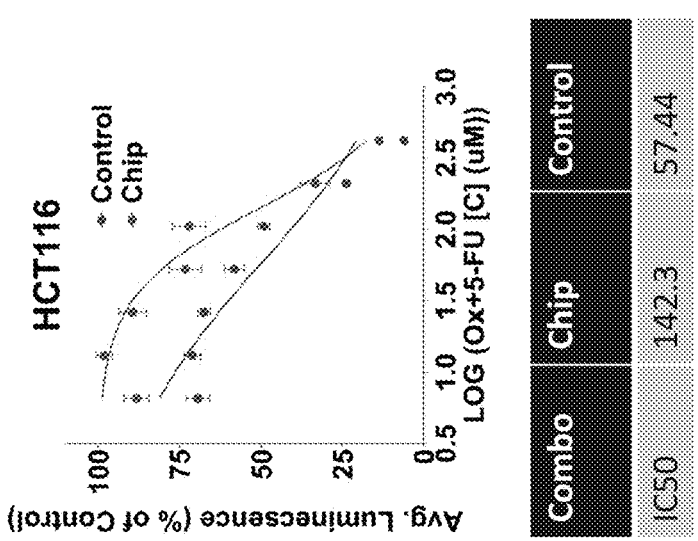
FIG. 15C is a graphical representation depicting the drug response of HCT116 cells, comparing a control system compared with the microfluidic systems described herein.
Figure 15B:
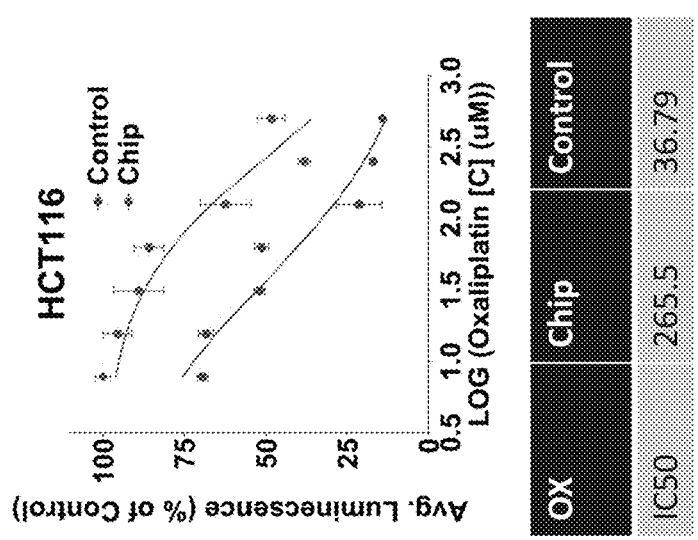
FIG. 15B is a graphical representation depicting the drug response of HCT116 cells, comparing a control system compared with the microfluidic systems described herein.
Figure 15A:
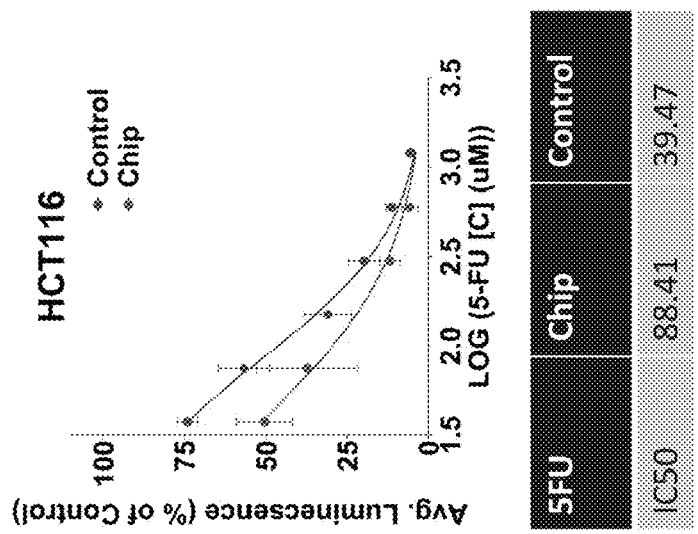
FIG. 15A is a graphical representation depicting the drug response of HCT116 cells, comparing a control system compared with the microfluidic systems described herein.

Similarly, FIGS. 15A-15C depict the drug response of platform 10 (labeled as Chip) compared with a static system (labeled as Control) for HCT116 tumoroid cells. The drug used in FIG. 15A is fluorouracil (5FU); the drug used in FIG. 15B is oxaliplatin (OX); and the drug used in FIG. 15C is a combination of oxaliplatin and fluorouracil in a 1:2.5 ratio. For each of the tests, platform 10 requires a higher drug dose to have the same IC50 as the static systems, other than for fluorouracil, which requires a lower drug dose.

SAW Based Sensor

Dysregulated pH is emerging as a hallmark of cancer because cancers show a 'reversed' pH gradient with a constitutively increased intracellular pH that is higher than the extracellular pH, which enables cancer progression by promoting proliferation (Kapus et al., 1993; Pouysségur et al, 1985; Stock and Schwab, 2009), the evasion of apoptosis (Lagadic-Grossmann et al., 2004; Matsuyama et al., 2000), metabolic adaptation (Chirstofk et al., 2008; Dietl et al., 2010; Kuwata et al., 1991), migration, and invasion (Ayad et al., 2008; Martin et al., 2010). An increased understanding of pH sensors is expected to provide insight into the molecular basis for pH-dependent tumor cell behaviors, information on the central role of pH sensors in tumor cell adaptations and assistance in assessing tumor drug response. However, the approaches to determining pH changes in long-term tumor or tumoroid cultures are limited. Specifically, a non-invasive, touch-free and real-time pH sensing as a research tool remains a major challenge to advancing tumor cell biology (Vonau et al., 2005).

Thus, the measurement of pH values is a key parameter in cell biology as it serves as an indicator of important changes to the status and growth phase of cell cultures. The traditional pH glass potentiometric (Shibata et al., 2013; Vonau et al., 2005) has limitations, such as limited shape, large size and mechanical fragility, making it difficult to integrate into microfluidic culture platforms. MEMS-based pH sensors have been widely studied, such as the ISFET pH sensor (Lu et al., 2018), capacitive pH sensor (Davidovikj et al., 2017), potentiometric pH sensor (Salazar et al., 2016), and conductimetric pH sensor (Y. Chen et al., 2013). The capacitive pH sensor is based on capacitive changes resulting from different concentrations of H+ and OH— in the solution (Shamsul Arefin et al., 2014). The capacitive sensor is not an ideal choice for solutions containing multiple types of ions where each ion changes the capacitance of the solution. The ISFET pH sensor is a more complex sensor design which measures the current flow through a small conduction channel between source and drain (Hizawa et al., 2007). The ISFET pH sensor requires very high power for FET operations and a sophisticated fabrication process. A conductimetric pH sensor can measure the conductivity of a pH-responsive layer such as hydrogel or other polymers (Korostynska et al., 2007). The polymer sensing layer swells or shrinks in response to hydration caused by the pH of a solution. This sensor requires current flow through the sensing layer which is not applicable to most in vivo studies. The drawback of the conductivity pH sensor is that it is not ion-selective, and it measures the combined effect of all ions in the sample solution.

Many researchers have reported different new potentiometric pH sensors based on varied materials and structures. It was found that the metal oxide electrodes, such as $TiO_2$, $RuO_2$, $IrO_2$ and ZnO, have responses towards different pH solutions (Fog and Buck, 1984; Gill et al., 2008; Usman Ali et al., 2011; Xu and Zhang, 2010). However, most of them require a large amount of sample solution and voltage applied to the surface in contact with the cell culture media. Surface plasmon resonance (SPR) based fiber optic sensors have been used as a novel device to detect the pH of small amounts of liquid (Mishra and Gupta, 2013; Prabhash et al., 2017; Singh and Gupta, 2012). The pH measured by SPR is the result of the refractive index changes which are caused by the swelling/shrinkage of the hydrogel layer in response to different pH values. This sensor has a short response reaction time, good stability and good sensitivity. However, it has some disadvantages, such as high cost, large complex structure, high sensitivity to shock and bulky design.

There are different types of acoustic waves commonly used as bio-sensors. These include Rayleigh wave, Lamb wave, shear horizontal wave (SH-SAW) (including Love wave), Quartz crystal microbalance (QCM) and Thin-film bulk acoustic resonator (FBAR) (Bunroddith et al., 2018; Chen et al., 2015; Hsu et al., 2009; Onen et al., 2012a; Pantazis et al., 2010). For biomedical in vivo sensor design, elimination of the current and voltage flow in the media is a critical issue which requires low power consumption and touch-free design between electrode and media. The acoustic wave-based sensor has these natural advantages compared to ISFET, capacitive, potentiometric and conductimetric pH sensors. The FBAR operates at a very high frequency which can also create an ultra-high sensitivity (D. Chen et al., 2013; Wang et al., 2014). However, the FBAR can only detect the mass loading including the mass density and viscosity but cannot directly detect the conductivity and permittivity changes in the sample loading (Chen et al., 2017, 2015). QCM can add a pH reactive polymer layer to measure the polymer mass loading by shrinkage and swell (Ayad et al., 2010; Jagur-Grodzinski, 2006). Quartz crystal microbalances (QCM) are the most-commonly used BAW devices which are fabricated by sandwiching a bulk piezoelectric material with top and bottom metallic electrodes. QCM can excite a bulk thickness shear wave which can be used in both dry and liquid applications. However, the sensitivity and resolution of the QCM pH sensor are relatively low compared to SAW FBAR device (Fu et al., 2017). The propagated wave energy of Rayleigh wave and Lamb wave sensors is distributed not only across the substrate surface but also into the substrate. This causes the Rayleigh and Lamb waves to be directly coupled with the media on top and damped by the mass loading, which makes these two types of wave insensitive to the mass changes in liquid sensing (Onen et al., 2012b). The SH-SAW is composed of interdigital fingers (IDTs) fabricated as periodic rectangular electrodes with uniform lengths and gaps. Electrical stimulation of these IDTs creates the SAW used for biosensing. The guided wave in the SH-SAW (Love wave) can be enhanced by the layer properties to further concentrate the wave energy on the substrate surface and thus increase the sensitivity of the device. The Love wave device can create a very high sensitivity level similar to FBAR device but at a low frequency (Fu et al., 2017). Due to the low damping coupling in a liquid environment, SH-SAW and Love wave devices have already been widely used as gas and liquid sensors due to their high accuracy, label-free, touch-free sensing and small volume sample consumption capabilities. ST-cut Quartz and 36° Y-cut $LiTaO_3$ are the two the most common substrates to generate SH-SAW. However, the electroacoustic coupling coefficient ($K^2$) of ST-cut Quartz (0.0016) is much smaller than that of 36° Y-cut $LiTaO_3$ (4.7) (Lam et al., 2004; Pang et al., 2013).

Zinc oxide (ZnO) is a relatively common material in piezoelectric and photoacoustic fields. Many SAW devices are coated with ZnO to increase sensitivity and reduce insertion loss (Chang et al., 2006; Powell et al, 2004). These devices are used for different applications such as pH sensors, UV sensors and biosensors. Iridium oxide ($IrO_2$) is a widely used material for pH MEMS sensors which can provide a rapid and stable response in different media because of its high conductivity (Kokooei et al., 2013). The sensing principle is based on the transition function of electrical corrosion between two oxidation states (Baur and Spaine, 1998):

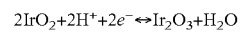

$$2IrO_2 + 2H^+ + 2e^- \leftrightarrow Ir_2O_3 + H_2O$$

In this study, the potential to enhance the sensitivity of oxide hydration changes to create a novel pH sensor with high sensitivity using a surface acoustic wave generation of a potential-distributed wave at the surface $IrO_2$ layer for longitudinal pH measurements in tumor cell cultures was investigated.

A 99.5% purity 2" diameter and 0.125" thick $IrO_2$ target bonded with cooper backplate and a 99.9% purity 2" diameter and 0.125" thick ZnO target bonded with cooper at backplate were purchased from AJA international Inc (MA, USA). 36° Y-cut X propagated $LiTaO_3$ wafers were purchased from University Wafer Inc (CA, USA) and two gain RF amplifiers (Olympus 5073PR and Olympus 5072PR) were purchased from Olympus NDT Inc (Santa Clara, CA, USA). A digit frequency counter Agilent 53220A was purchased from Agilent Technologies Inc (Santa Clara, CA, USA) and an oscillator Tektronix TS2001C was purchased from Tektronix Inc (Beaverton, OR, USA). BenchVue Universal Counter software was licensed by Keysight Technologies (Santa Clara, CA, USA). H460 cell line was purchased from American Type Culture Collection (Manassas, VA, USA). HyClone™ RPMI 1640 culture media was purchased from GE Healthcare Life Sciences (Pittsburgh, PA, USA). Commercial pH meter was purchased from Denver Instrument (Co, USA). Standard pH buffer solution was purchased from Sigma-Aldrich (WI, USA), Slygard® 184 Silicone Elastomer kit was purchased from Dow Corning Inc (MI, USA). Hoechst 33342 was purchased from NucBlue, Life Technologies (MA, USA).

Before the fabrication, a guide layer sensitivity comparison between ZnO and $IrO_2$ was investigated by using the wave perturbation theory. A thorough parametric study on sensitivity and perturbation was done for ZnO and $IrO_2$. The results were compared to optimize the design. The wave transmission study was based on a full time-dependent analysis to obtain the dynamic response of the impulse signal simulated devices in order to study the electrical perturbation on the substrate surface and find the limitation of the device. The final layer thickness was varied to balance the sensitivity and the wave transmission reflection ratio. Then the IDTs were fabricated by microfabrication techniques with feature parameters listed in Table 1 (see FIG. 22). Further detail on the fabrication process can be found in an earlier publication (Guldiken et al., 2012). The ZnO film was deposited by an RF sputtering system at a deposition rate of about 120 nm per hour under a low substrate temperature of 180° C., with 6 sccm Ar and 6 sccm $O_2$, and a 100 W RF power. The $IrO_2$ thin film was also deposited by RF sputtering. Prior to deposition, the chamber was pumped down to $1\times10^{-8}$ Torr. The substrates for sputtering substrates were 36 Y-cyt propagated lithium tantalate with transducer features on top (chrome layer 100 nm). Sputtering was performed in a pure Ar environment with a lower RF power of 80 W to mitigate potentially damaging bombardment of the growing $IrO_2$ film. Room temperature was used, which generates lower stress on the surface of lithium tantalate piezoelectric material since the $IrO_2$ is a conductive metal oxide.

For growing cell tumoroid cultures, a fiber-inspired smart scaffold (FiSS) was used that was internally-developed, which generates tumor-like organoids from seeded tumor cells, hence called tumoroids. FiSS was prepared by electrospinning (Girard et al., 2013). FiSS was placed into a 6-well plate and 200,000 H460 lung cancer cells were seeded into each well in RPMI media containing 10% fetal bovine serum and 1% penicillin-streptomycin. Media (7 mL) was used in each well and cells were cultured on the scaffold for six days. Successful growth of cells on 3D scaffold as tumoroids was confirmed by staining the cells with Hoechst 33342 and then capturing images using fluorescence microscopy.

H460 human lung adenocarcinoma cells were maintained in RPMI media containing 10% fetal bovine serum (FBS) and 1% penicillin-streptomycin. All cells were cultured in 6 well plates in a humidified incubator at 37° C. in a 5% $CO_2$ atmosphere. 1 mL of cell media supernatant in total was collected from a different well each day from day 0 to day 5. Half a minute after the frequency counter started to record, 100 µL of each culture media was placed on the test well of the chip and 100 µL of fresh culture media was taken from the same incubator and placed on the control well to record the relative frequency response for a duration of 10 min. A standard laboratory potentiometric pH meter was calibrated with standard pH buffer solution and then cleaned prior to each measurement of cell culture media at the same time to compare the pH value from the device. After recording each sample, the cell suspension was removed and the well was washed with three changes of PBS followed by three changes of water to clean the sensing area.

Figure 16:
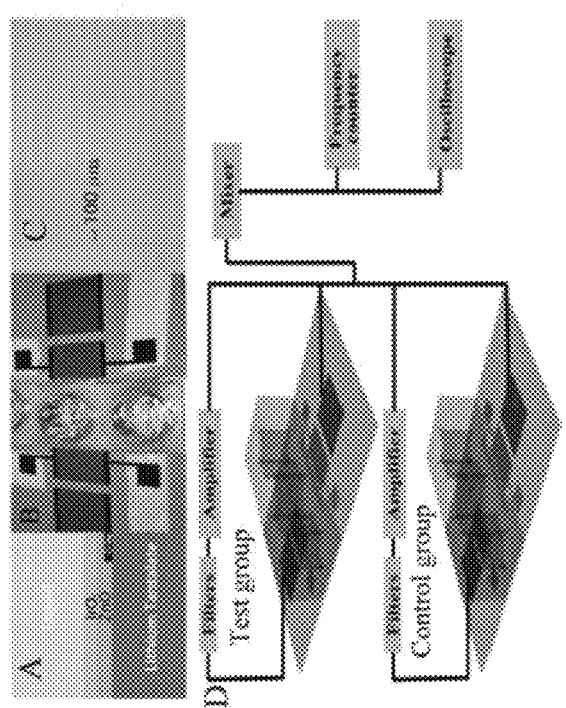
FIG. 16 depicts a SAW based sensor. Section A is a view of the double guide layer of SAW based sensor. Section B depicts a fabricated and assembled resonator and fluidic well. Section C depicts finger pairs under a microscope. Section D depicts an experimental setup.

The frequency changes were measured by comparing the frequency shift between the test group to the control group as shown in FIG. 16. During the experiments, the frequency counter measures the frequency shift in two groups at the same time and transfers the real-time data to the computer. With the help of the BenchVue software, a programmed data flow process handles the 6 data points generated by each group every second. The software records and plots the control group recorded frequency ($f_c$) minus the test group recorded frequency ($f_T$) then divided by the control group recorded frequency. From the perturbation theory, when the Love waves propagate through the sensing area, the phase velocity changes due to the mass loading changes at the surface of the $IrO_2$ and the conductivity of the cell media in the equations below. The data is then sorted and plotted out in normalized relative frequency shift.

Change in velocity:

$$\frac{\Delta V}{V} = \frac{\Delta f}{f} = \frac{f_c - f_T}{f_c} = \frac{K_s^2}{2} \frac{(\sigma_1/\omega)^2 + (\varepsilon_1 - \varepsilon_{REF})(\varepsilon_1 + \varepsilon_{PIEZO})}{(\sigma_1/\omega)^2 + (\varepsilon_1 + \varepsilon_{PIEZO})^2}$$

Change in attenuation:

$$\frac{\Delta \alpha}{k} = \frac{K_s^2}{2} \frac{(\sigma_1/\omega)(\varepsilon_{REF} + \varepsilon_{PIEZO})}{(\sigma_1/\omega)^2 + (\varepsilon_1 + \varepsilon_{PIEZO})^2}$$

A numerical method was designed to optimize the thickness of the $IrO_2$ and ZnO thin film layer as a guiding layer. The mathematical model was based on previous reports from the perturbation analysis model (McMullan et al., 2000; Onen and Guldiken, 2014). The substrate and the guiding layers were assumed to be elastic and isotropic materials without significant electrical perturbation. The analysis is based on the dispersion equation and sensitivity equation verified by McHale et al. (2002) which depends on the dispersion curve, guiding and perturbing mass layer properties (Onen, 2013). Other leaky properties of SH or SSBW waves were also neglected, since only the Love waves were effective in energy confinement to the surface. The analysis was performed with the nondimensional thickness (z) defined as $z = d_g \cdot f/v_g^\infty$, where $d_g$ is the thickness, f is the frequency, and $v_g^\infty$ is the shear velocity in guiding layer. Shear horizontal polarized wave propagation was investigated step by step by dispersion solution and perturbation analysis (McMullan et al., 2000; Onen and Guldiken, 2014).

Figure 17:
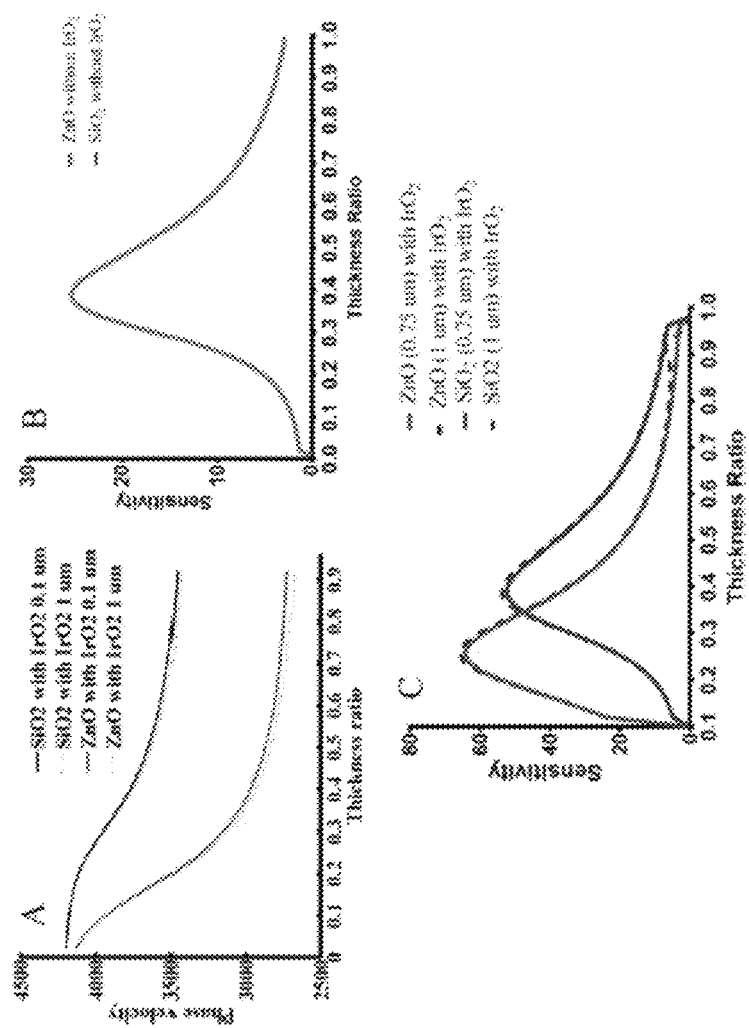
FIG. 17 includes graphical representations of phase velocity and sensitivity compared to a thickness ratio for embodiments of the present invention. Section A depicts a dispersion curve with $SiO_2/IrO_2$ and $ZnO/IrO_2$ guiding layer at 14.0 MHz. Section B depicts a perturbation analysis method to calculate the sensitivity of multiple layers SAW-based sensor. At the single layer mode, the sensitivity of the $SiO_2/LiTaO_3$ is almost the same as $ZnO/LiTaO_3$ device. Section C illustrates that the $IrO_2/ZnO/LiTaO_3$ create higher sensitivity with thin layer thickness requirement compared to $IrO_2/SiO_2/LiTaO_3$.

The comparison of the ZnO and $SiO_2$ layer sensitivity on the device is shown in FIG. 17. Section A of FIG. 17 illustrates the dispersion curve of two different guiding layers with the same top layer of $IrO_2$. The $SiO_2$ dispersion curves have smoother transition regions and lower slopes. The lower slopes illustrate a smaller velocity difference between the substrate and guiding layer which results in lower sensitivity (Onen and Guldiken, 2014). Section B of FIG. 17 shows the device model with a fluid layer and a single pure guide layer on top of the substrate (Liquid/ZnO/$LiTaO_3$ and Liquid/$SiO_2$/$LiTaO_3$). This figure shows that the $SiO_2$ and $IrO_2$ have similar sensitivity at the same thickness ratio (film thickness divided by wavelength) with the peak sensitivity at thickness ratio (guide layer thickness/wavelength) $\varepsilon$=0.42. But after the $IrO_2$ layer is deposited on top of the ZnO layer, the ZnO layer revealed two advantages compared to $SiO_2$. Section C of FIG. 17 shows that ZnO has higher sensitivity than the $SiO_2$ layer and it also reduced the layer thickness requirement to reach maximum sensitivity by almost half ($\varepsilon_{ZnO}$=0.24, $\varepsilon_{SiO2}$=0.42). ZnO significantly reduced the layer thickness requirement to create high sensitivity for the device. From these results, the maximum sensitivity is created at the thickness ratio of ZnO equal to 0.24 with almost 2-fold sensitivity compared to the pure ZnO guiding layer's maximum sensitivity peak. However, the perturbation analysis is based on the theory of a linear elastic model with lossless substrate and it is hard to show the electric perturbation on the surface.

Acoustic propagation mass sensing within multi-thin-layer systems is essential for optimization of gravimetric sensors. Perturbation analysis is an easy method to set up a simplified model. The actual wave propagation problem on the piezoelectric substrate involves an anisotropy layer, piezoelectricity, and three-dimensional wave diffraction. It is very complicated and not feasible for numerical methods to model all of these features. It is also not possible for numerical methods to analyze the electrical properties of the wave mode such as velocity phase, electrical perturbation, and wave transmission. The finite element method provides a more suitable method to analyze the wave trans-mission and electrical perturbation. The deposited ZnO is a piezoelectric guiding layer for this Love device, and the $IrO_2$ thin layer on top of ZnO works as both a guiding layer and pH sensitive layer. Due to the conductive properties of the metal oxide $IrO_2$, the conductivity of the $IrO_2$ and the media on top of the layer will affect the electrical perturbation on the guiding layer. Additionally, the electric equilibrium reaction at the surface will affect both the conductivity and the mass loading.

A COMSOL finite element model was built to simulate the wave propagation properties including the wave transmission, mass loading limitation and electrical perturbation on the substrate in FIG. 18. The simplified 3D model consists of a two-port resonator design with a ZnO thin layer and $IrO_2$ thin layer on top of a Lithium tantalate substrate with 4 mesh nodes per wavelength. The mesh consisted of 47,352 domain elements, 24,734 boundary elements and 2412 edge elements. The total number of nodes is 926,222 as shown in section A of FIG. 18. A time-dependent analysis was conducted to calculate the response from the interdigital output finger with a short impulse signal. The total sampling time for the whole simulation was 4400 ns (nano second) with a sampling frequency of 1000 MHz. The impulse voltage was applied to the input electrodes while $V_+$ and $V_-$ were applied to the even and odd fingers.

Sections B, C, and D of FIG. 18 show the electrical potential distribution at the surface of the device and the mechanical surface wave's electrical propagation along the detection area from 0 ns to 1500 ns. The simulation results in sections E and F of FIG. 18 were verified by the fabricated device. In section E, the simplified 3D model with 100 nm Cr IDTs, 500 nm ZnO and 30 nm $IrO_2$ layer matches the physical device's first two wave modes with peaks of 13.907 MHz and 15.34 MHz. However, due to the simplified 3D simulation model with only one single pair of input/output interdigital fingers and one reflecting finger for each side, the third and fourth mode of the wave is not perfectly matched with the experimental results. The mechanical wave phase velocity is affected by the mass loading and electrical properties of the surface and media. The simulation results show that the surface acoustic wave energy loss increases at the surface when the thickness of the $IrO_2$ thin layer increases as compared in sections E and F of FIG. 18. The surface acoustic wave is damped by the $IrO_2$ thin layer and starts to cease propagation at a thickness of 70 nm, as shown in section E. Section F shows that at the increased thickness of $IrO_2$ device of 70 nm compared to the thickness 30 nm in section E, the transmission ratio reduces from −32.6 dB to −37 dB. The experimental device reduces the transmission ratio from −30.8 dB to −50.3 dB. The simulation results match the experiment results in section F. However, the transmission ratio is 13.3 higher than the experiment. The operation frequency of the device slightly decreases as the thickness of the $IrO_2$ increases both in the simulation results and experiment results in section F and in section G. The mass loading changes at the surface of the $IrO_2$ layer result in the phase velocity and frequency shift. In section H, the simulation results illustrate that if the $IrO_2$ mass loading even slightly increases from 1 ng to 2 ng, the frequency decreases and the insertion loss goes down.

Figure 19:
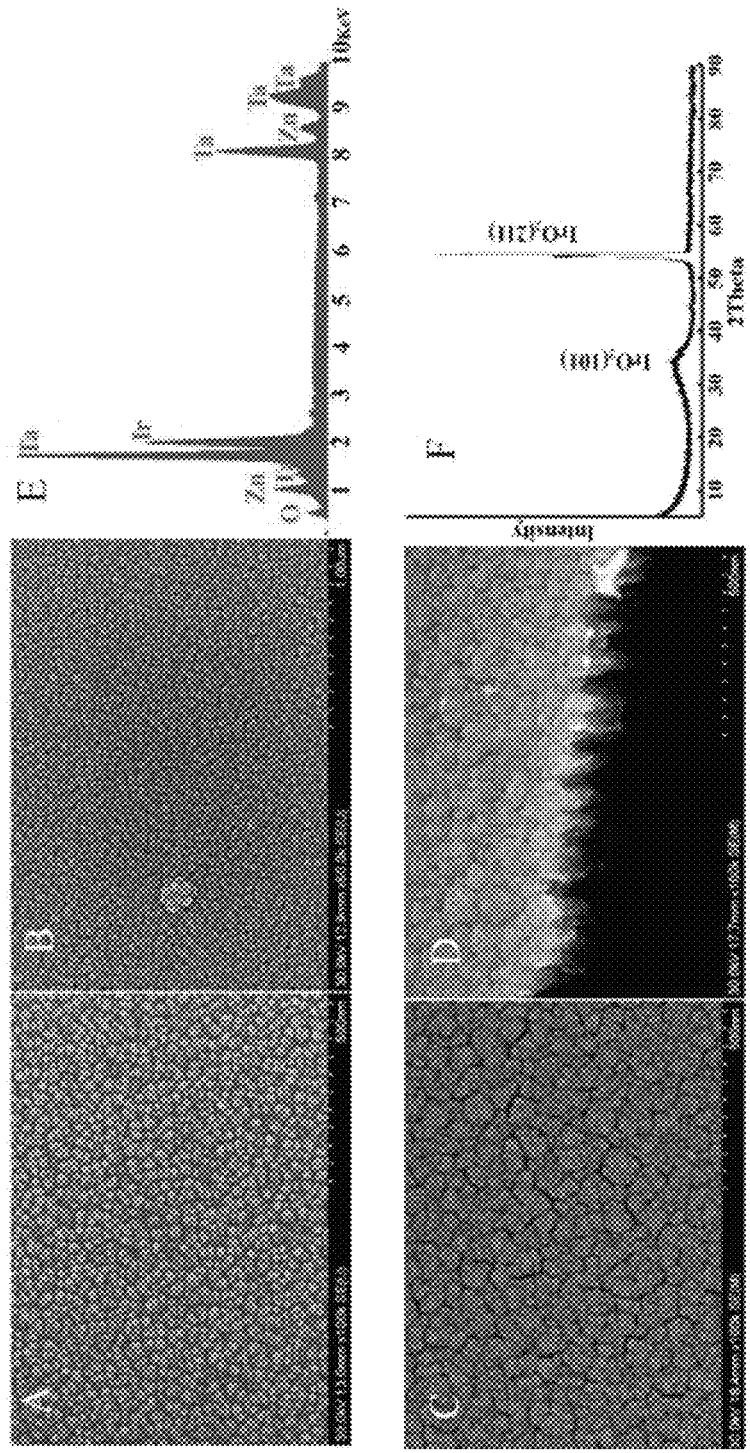
FIG. 19 depicts a SEM surface topographical image of a ZnO thin film in section A. Sections B, C, and D illustrate SEM surface topographical image of a $IrO_2$ thin film. Section E depicts an EDS diffraction analysis of the device. Section F is an XRD diffraction analysis of the device to find the 2theta for the $IrO_2$ thin layer.

After the device was fabricated, the SEM, XRD, and EDS images were captured to investigate the morphology of the ZnO and $IrO_2$ layers as illustrated in FIG. 19. Section A of FIG. 19 is an SEM surface topographical image at 100 K magnification of a ZnO thin film with thermal annealing at 300° C. The image shows that the surface of the RF deposited ZnO thin flat film layer. Section B and section C of FIG. 19 are topographical images at 50 K and 100 K magnification of the $IrO_2$ thin film layer. Section D is the cross-section view of the $IrO_2$ layer. Sections E and F are the EDS and XRD diffraction analysis of the device with ZnO and $IrO_2$ thin film layer. The $IrO_2$ has two peaks with 2theta at 34.7° and 54.3°.

Electrical perturbation occurs due to interactions between the electrical potential and the liquid. It is also referred to as acoustoelectric interaction. The properties of the liquid that contribute to electrical perturbation are the conductivity ($\sigma$) and the permittivity ($\varepsilon$). The conductivity of the sampling solution is also related to frequency shift from the change in velocity and change in attenuation equations. The SAW propagated with multiple fluxes of momentum energy on the surface of $IrO_2$. The momentum will reduce to become a force on the electron which is also referred to as acoustoelectric interaction. For the acid region, the conductivity of the film decreases the result of the interaction as the pH value increase. From the change in attenuation equation, a larger Q leads to a smaller phase velocity. Thus, the conductivity of the media layer increases as the phase velocity decreases. The resonant frequency of the propagated SAW is relative to the phase velocity at a fixed wavelengths device. Therefore, a decrease of the resonant frequency of the device should be detected on low pH media. In the change in velocity equation, when the pH value decreases, it will result in more $IrO_2$ translating to $Ir_2O_3$, which will slightly decrease the mass of the $IrO_2$ layer and slightly increase the frequency as shown in the simulation results of section H. There is only maximum ~1.7 ng mass changes if all the $IrO_2$ translates to the $Ir_2O_3$ in the detection well. In the simulation results of section H, 2 ng mass changes lead to less than 400 Hz shift. The shifts of charge distribution on ZnO layer caused by changes in $IrO_2$ layer's electrical properties dominate the phase velocity changes. Similar analysis shows the expected results in the alkaline region, as the interaction between hydroxide and metal oxide layer ($IrO_2$ and ZnO) also enhances the guiding layer conductivity (Qiu et al., 2011).

Figure 20:
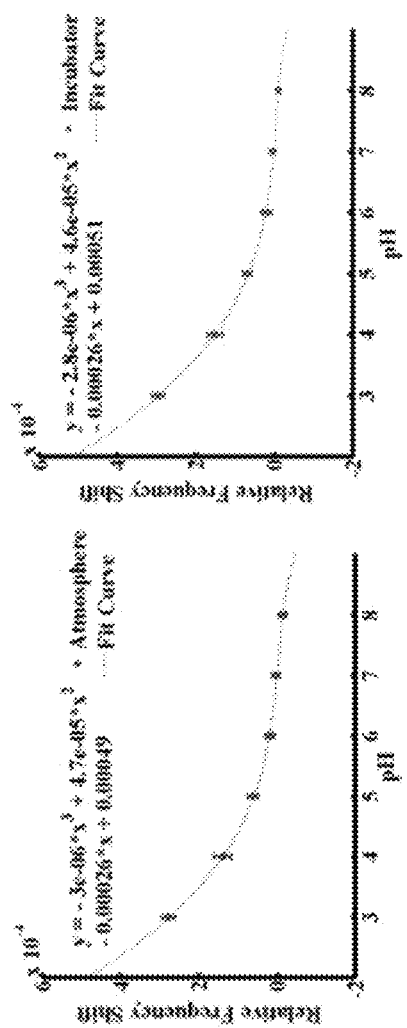
FIG. 20 illustrates the SAW-based sensor tested by standard pH solutions to record the frequency response. Since the $CO_2$ concentration and temperature will affect the pH, pH is measured both inside incubator and at atmosphere.

A standard pH buffer solution was prepared to calibrate the response of the device to different pH solutions both inside the incubator and at atmosphere outside the incubator. The $CO_2$ level and temperature inside the incubator affect the pH and function of the device. The device calibration determines the relationship of the relative frequency shift to standard pH value both in the incubator and at atmosphere. The change in $IrO_2$ relative permittivity and electrical conductivity due to the metal oxide corrosion on the surface will result in the phase velocity of the propagated wave shift. As discussed previously, the relative frequency shift is equal to the frequency of the reference device minus the working device divided by the reference frequency. The operation frequency of the working device decreases as the pH value decreases as both the relative permittivity and the electric conductivity increase. The relationship between the pH value and frequency shift is nonlinear due to the nonlinear change of the conductivity and mass loading which shows the polynomial fit curve in FIG. 20. Both the fit curves for atmosphere and incubator environment have the $R^2=0.99$. At pH 3, the device has a maximum frequency shift of 0.296 ppm (0.000296). The frequency shift at atmosphere is larger than the shift inside the incubator which is to be expected. The relationship between the standard pH value and the relative frequency shift provides the conversion equation to convert the relative frequency to pH value for cell culture experiments.

Figure 21:
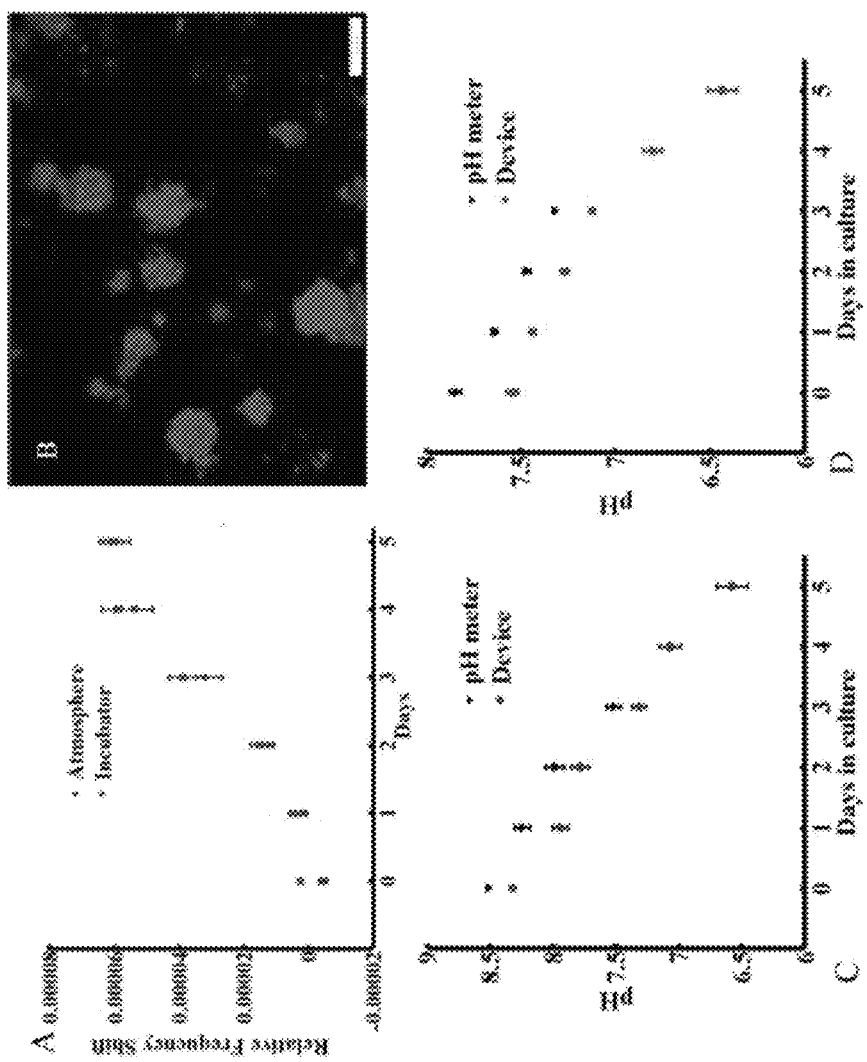
FIG. 21 depicts the relative frequency response of the device to cell culture media in different days both in atmosphere and incubator measurements in section A. Section B depicts Day 5 H460 tumoroids on scaffold stained with Hoechst. Section C illustrates the comparison between the commercial pH meter measured cell media pH value and device measured value at atmosphere from day 0 to day 5. Section D illustrates the comparison between the commercial pH meter measured cell media pH value and device measured value inside the incubator from day 0 to day 5.

After the pH value of the standard solution is recorded, a pH value of cell culture media is measured from day 0 to day 5. The frequency shift from day 0 to day 1, day 4 to day 5 is much smaller than the frequency shift from day 2 to day 3, from day 3 to day 4. A maximum 0.0591 ppm (0.0000591) was measured at day 5 as illustrated in section A of FIG. 21. Additionally, the relative frequency shift on the y-axis in section A of FIG. 21 is converted to standard pH value by the relationship in FIG. 20 and replotted in section C of FIG. 21 (atmosphere) and section D of FIG. 21 (incubator). The cell media from day 0 to day 5 was also measured by commercial instrument and compared to the $IrO_2/ZnO/LiTaO_3$ device in sections C-D of FIG. 21. It was found that the SAW acoustic device measured pH value was 1.0-3.05% smaller than the value from the commercial device value at atmosphere, and 2.25-3.75% smaller than the value from the commercial device value inside the incubator. This discrepancy could be caused by several factors. First, the conversion from the average frequency shift to standard pH includes a calculation error. Second, the cell culture media from day 1 to day 5 is slightly different than unused cell media on the working device in its mechanical and electrical properties such as density and dielectric constant. Third, the ZnO layer may contribute an effect to the phase velocity of the device. The $ZnO/LiTaO_3$ SAW-based (500 nm ZnO layer) device without $IrO_2$ layer is tested by standard pH solutions at atmosphere to record the frequency response. Without the $IrO_2$ layer, the ZnO sensitivity is quite low compared to the device with $IrO_2$ layer shown in FIG. 20.

The experiment results show the advantage of the unique design by using multiple layers. The ZnO layer works as a guiding layer helping the wave propagation to concentrate energy and charge potential at ZnO layer which increases the sensitivity of the device. ZnO also works as a dielectric shield layer between the IDT fingers and $IrO_2$ conductive layer. The most important feature is that waves propagating at the ZnO intermediate layer can be easily affected by changes in electrical properties through the conductive $IrO_2$ layer. Therefore, piezoelectric surface charge and the voltage potential at the ZnO layer will be affected by the $IrO_2$ layer's chemical reaction and charges. The design herein was compared to other acoustic-based pH sensors in Table 2 (shown in FIG. 23). The device based on the bare ZnO layer has a little high sensitivity by etching the surface ZnO, which has stability and repeatability issues and can only be used for the disposable device.

In this study, a multi-layer guided surface acoustic wave sensor was investigated theoretically and experimentally in detail for pH bio-sensing. Shear horizontal layer guided surface acoustic wave (SAW) device sensitivity and capability was modeled using perturbation analysis mode and finite element method. The model was verified experimentally, and a surface acoustic wave pH biosensor study was presented. A novel pH sensor based on 13.91 MHz center frequency SAW device was coated with ZnO and $IrO_2$ guided and sensitization layers to increase sensitivity. The change in conductivity of ZnO and $IrO_2$ induced by pH solutions affects SAW phase velocity and attenuation. By measuring the frequency shift induced by a change in SAW phase velocity between the work group and control group, the pH value in a target cell culture media can be determined. To improve the sensitivity and stability of the sensor, multiple methods to fabricate the ZnO layer on shear horizontal wave devices were compared. The results of experiments show the potential application of this device to be integrated with microfluidic channels used in cancer biology and in regenerative medicine.

REFERENCES

Ayad, M. M., Salahuddin, N. A., Abou-Seif, A. K., Alghaysh, M. O., 2008. PH sensor based on polyaniline and aniline-anthranilic acid copolymer films using quartz crystal micro-balance and electronic absorption spectroscopy. Polym. Adv. Technol. 19, 1142-1148.

Ayad, M. M., Salahuddin, N. A., Alghaysh, M. O., Issa, R. M., 2010. Phosphoric acid and pH sensors based on polyaniline films. Curr. Appl. Phys. 10, 235-240.

Baur, J. E., Spaine, T. W., 1998. Electrochemical deposition of iridium(IV) oxide from alkaline solutions of iridium (III) oxide. J. Electroanal. Chem. 443, 208-216.

Bunroddith, K., Viseshakul, N., Chansiri, K., Lieberzeit, P., 2018. QCM-based rapid detection of PCR amplification products of *Ehrlichia canis*. Anal. Chim. Acta 1001, 106-111.

Chang, R. C., Chu, S. Y., Hong, C. S., Chuang, Y. T., 2006. A study of love wave devices in ZnO/quartz and ZnO/$LiTaO_3$ structures. Thin Solid Films 498, 146-151.

Chen, D., Wang, J., Wang, P., Guo, Q., Zhang, Z., Ma, J., 2017. Real-time monitoring of human blood clotting using a lateral excited film bulk acoustic resonator. J. Micromech. Microeng. 27, 045013.

Chen, D., Wang, J., Xu, Y., Li, D., Zhang, L., Li, Z., 2013. Highly sensitive detection of organophosphorus pesticides by acetylcholinesterase-coated thin film bulk acoustic resonator mass-loading sensor. Biosens. Bioelectron. 41, 163-167.

Chen, G., Zhao, X., Wang, X., Jin, H., Li, S., Dong, S., Flewitt, A. J., Milne, W. I., Luo, J. K., 2015. Film bulk acoustic resonators integrated on arbitrary substrates using a polymer support layer. Sci. Rep. 5, 1-8.

Chen, Y., Mun, S. C., Kim, J., 2013. A wide range conductometric pH sensor made with titanium dioxide/multiwall carbon nanotube/cellulose hybrid nanocomposite. IEEE Sens. J. 13, 4157-4162.

Christofk, H. R., Vander Heiden, M. G., Wu, N., Asara, J. M., Cantley, L. C., 2008. Pyruvate kinase M2 is a phosphotyrosine-binding protein. Nature 452, 181-186.

Davidovikj, D., Scheepers, P. H., van der Zant, H. S. J., Steeneken, P. G., 2017. Static capacitive pressure sensing using a single graphene drum. ACS Appl. Mater. Interfaces 9, 43205-43210.

Dietl, K., Renner, K., Dettmer, K., Timischl, B., Eberhart, K., Dorn, C., Hellerbrand, C., Kastenberger, M., Kunz-Schughart, L. A., Oefner, P. J., Andreesen, R., Gottfried, E., Kreutz, M. P., 2010. Lactic acid and acidification inhibit TNF secretion and glycolysis of human monocytes. J. Immunol. 184, 1200-1209.

Fog, A., Buck, R. P., 1984. Electronic semiconducting oxides as pH sensors. Sens. Actuators 5, 137-146.

Fu, Y. Q., Luo, J. K., Nguyen, N. T., Walton, A. J., Flewitt, A. J., Zu, X. T., Li, Y., McHale, G., Matthews, A., Iborra, E., Du, H., Milne, W. I., 2017. Advances in piezoelectric thin films for acoustic biosensors, acoustofluidics and lab-on-chip applications. Prog. Mater. Sci. 89, 31-91.

Gill, E., Arshak, K., Arshak, A., Korostynska, O., 2008. Mixed metal oxide films as pH sensing materials. Microsyst. Technol. 14, 499-507.

Girard, Y. K., Wang, C., Ravi, S., Howell, M. C., Mallela, J., Alibrahim, M., Green, R., Hellermann, G., Mohapatra, S. S., Mohapatra, S., 2013. A 3D fibrous scaffold inducing tumoroids: a platform for anticancer drug development. PLoS One 8.

Guldiken, R., Jo, M. C., Gallant, N. D., Demirci, U., Zhe, J., 2012. Sheathless size-based acoustic particle separation. Sensors 12, 905-922.

Hizawa, T., Matsuo, J., Ishida, T., Takao, H., Abe, H., Sawada, K., Ishida, M., 2007. 32×32 pH image sensors for real time observation of biochemical phenomena. In: Proceedings of the 4th International Conference on Solid-State Sensors, Actuators and Microsystems TRANSDUCERS and EUROSENSORS '07, IEEE, pp. 1311-1312.

Hsu, C. L., Shen, C. Y., Tsai, R. T., Su, M. Y., 2009. Surface acoustic wave ammonia sensors based on ST-cut quartz under periodic al structure. Sensors 9, 980-994.

Jagur-Grodzinski, J., 2006. Nanostructured polyolefins/clay composites: role of the molecular interaction at the interface. Polym. Adv. Technol. 17, 395-418.

Kakooei, S., Ismail, C., Ari-Wahjoedi, B., 2013. An overview of pH sensors based on Iridium oxide: fabrication and application. Int. J. Mater. Sci. Innov. 1, 62-72.

Kapus, A., Romanek, R., Qu, A. Y., Rotstein, O.D., Grinstein, S., 1993. A pH-sensitive and voltage-dependent proton conductance in the plasma membrane of macrophages. J. Gen. Physiol. 102, 729-760.

Korostynska, Olga, Arshak, Khalil, Gill, Edric, Arshak, Arousian, 2007. Review on key laboratory State-of-the-art in nonlinear mechanics polymer based pH mechanics, Sensors sciences. Sensors 7 (12), 3027-3042.

Kuwata, F., Suzuki, N., Otsuka, K., Taguchi, M., Sasai, Y., Wakino, H., Ito, M., Ebihara, S., Suzuki, K., 1991. Enzymatic regulation of glycolysis and gluconeogenesis in rabbit periodontal ligament under various physiological pH conditions. J. Nihon Univ. Sch. Dent. 33, 81-90.

Lagadic-Gossmann, D., Hue, L., Lecureur, V., 2004. Alterations of intracellular pH homeostasis in apoptosis: origins and roles. Cell Death Differ. 11, 953-961.

Lam, C. S., 2010. A review of the recent development of temperature stable cuts of quartz for SAW applications. Epson Appl. Notes White Papers.

Lu, C.-H., Hou, T.-H., Pan, T.-M., 2018. High-performance double-gate α-InGaZnO ISFET pH sensor using a $HfO_2$ gate dielectric. IEEE Trans. Electron Devices 65, 237-242.

Martin, N. K., Gaffney, E. A., Gatenby, R. A., Maini, P. K., 2010. Tumour-stromal interactions in acid-mediated invasion: a mathematical model. J. Theor. Biol. 267, 461-470.

Matsuyama, S., Llopis, J., Deveraux, Q. L., Tsien, R. Y., Reed, J. C., 2000. Changes in intramitochondrial and cytosolic pH: early events that modulate caspase activation during apoptosis. Nat. Cell Biol. 2, 318-325.

McMullan, C., Mehta, H., Gizeli, E., Lowe, C. R., 2000. Modelling of the mass sensitivity of the Love wave device in the presence of a viscous liquid. J. Phys. D. Appl. Phys. 33, 3053-3059.

McHale, G., Newton, M. I., Martin, F., 2002. Theoretical mass, liquid, and polymer sensitivity of acoustic wave sensors with viscoelastic guiding layers. J. Appl. Phys. 93 (1), 675-690.

Mishra, S. K., Gupta, B. D., 2013. Surface plasmon resonance based fiber optic pH sensor utilizing Ag/ITO/Al/hydrogel layers. Analyst 138, 2640-2646.

Onen, O., Ahmad, A. A., Guldiken, R., Gallant, N. D., 2012a. Surface modification on acoustic wave biosensors for enhanced specificity. Sensors 12, 12317-12328.

Onen, O., Guldiken, R., 2014. Investigation of guided surface acoustic wave sensors by analytical modeling and perturbation analysis. Sens. Actuators A Phys. 205, 38-46.

Onen, O., Sisman, A., Gallant, N. D., Kruk, P., Guldiken, R., 2012b. A urinary Bcl-2 surface acoustic wave biosensor for early ovarian cancer detection. Sensors 12, 7423-7437.

Onen, Onursal, 2013. Analytical Modeling, Perturbation Analysis and Experimental Characterization of Guided Surface Acoustic Wave Sensors". Graduate Theses and Dissertations.

Pang, H. F., Fu, Y. Q., Li, Z. J., Li, Y., Ma, J. Y., Placido, F., Walton, A. J., Zu, X. T., 2013. Love mode surface acoustic wave ultraviolet sensor using ZnO films deposited on 36° Y-cut $LiTaO_3$. Sens. Actuators A Phys. 193, 87-94.

Pantazis, A. K., Gizeli, E., Konstantinidis, G., 2010. A high frequency GaN Lamb-wave sensor device. Appl. Phys. Lett. 96, 194103.

Pouysségur, J., Franchi, A., L'Allemain, G., Paris, S., 1985. Cytoplasmic pH, a key determinant of growth factor-induced DNA synthesis in quiescent fibroblasts. FEBS Letters 190 (1), 115-119.

Powell, D. A., Kalantar-Zadeh, K., Wlodarski, W., 2004. Numerical calculation of SAW sensitivity: application to $ZnO/LiTaO_3$ transducers. Sens. Actuators A Phys. 115, 456-461.

Prabhash, P. G., Haritha, V. S., Nair, S. S., Pilankatta, R., 2017. Localized surface plasmon resonance based highly sensitive room temperature pH sensor for detection and quantification of ammonia. Sens. Actuators B Chem. 240, 580-585.

Qiu, X., Tang, R., Chen, S. J., Zhang, H., Pang, W., Yu, H., 2011. PH measurements with ZnO based surface acoustic wave resonator. Electrochem. Commun. 13, 488-490.

Salazar, P., Garcia-Garcia, F. J., Yubero, F., Gil-Rostra, J., González-Elipe, A. R., 2016. Characterization and application of a new pH sensor based on magnetron sputtered porous WO3 thin films deposited at oblique angles. Electrochim. Acta 193, 24-31.

Shamsul Arefin, M., Bulut Coskun, M., Alan, T., Neild, A., Redoute, J.-. M., Yuce, M. R., 2014. A MEMS capacitive pH sensor for high acidic and basic solutions. In: Proceedings of the IEEE SENSORS 2014, 1792-1794.

Shibata, M., Kato, M., Iwamoto, Y., Nomura, S., Kakiuchi, T., 2013. Potentiometric de-termination of pH values of dilute sulfuric acid solutions with glass combination electrode equipped with ionic liquid salt bridge. J. Electroanal. Chem. 705, 81-85.

Singh, S., Gupta, B. D., 2012. Fabrication and characterization of a highly sensitive surface plasmon resonance based fiber optic pH sensor utilizing high index layer and smart hydrogel. Sens. Actuators B Chem. 173, 268-273.

Srivastava, J., Barber, D. L., Jacobson, M. P., 2007. Intracellular pH sensors: design principles and functional significance. Physiology 22, 30-39.

Stock, C., Schwab, A., 2009. Protons make tumor cells move like clockwork. Pflug. Arch. Eur. J. Physiol. 458, 981-992.

Usman Ali, S. M., Alvi, N. H., Ibupoto, Z., Nur, O., Willander, M., Danielsson, B., 2011. Selective potentiometric determination of uric acid with uricase immobilized on ZnO nanowires. Sens. Actuators B Chem. 152, 241-247.

Vonau, W., Gabel, J., Jahn, H., 2005. Potentiometric all solid-state pH glass sensors. Electrochim. Acta 50, 4981-4987.

Wang, J., Chen, D., Xu, Y., Liu, W., 2014. Label-free immunosensor based on micro-machined bulk acoustic resonator for the detection of trace pesticide residues. Sens. Actuators B Chem. 190, 378-383.

Xu, Bin, Zhang, Wei-De, 2010. Modification of vertically aligned carbon nanotubes with $RuO_2$ for a solid-state pH sensor. Electrochim. Acta 55 (8), 2859-2864.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A method of anticancer drug screening, the method comprising the steps of:
    adding a plurality of target cells onto a fiber inspired smart scaffold to a culture well of a microfluidic platform, the microfluidic platform comprising
        a plate including a plurality of bottomless wells coupled to a chip insert including a plurality of bioreactors by inserting the chip insert below the plate, such that the plurality of bioreactors are in communication with the plurality of bottomless wells, each of the plurality of bioreactors including a culture well in fluidic communication with each of an inlet well and an outlet well;
    adding a first amount of a culture media to the inlet well, adding a second amount of the culture media to the culture well, and adding a third amount of the culture media to the outlet well, the first amount being greater than each of the second amount and the third amount;
    flowing the culture media from the inlet well toward the outlet well via the culture well due to the difference in volume between the inlet well and the outlet well;
    after approximately 48 hours, adding an amount of a testing drug to the fiber inspired smart scaffold; and
    quantifying viability of the plurality of target cells after the amount of the testing drug is added to the scaffold;
    wherein a decreased number of the plurality of target cells on the fiber inspired smart scaffold is indicative of decreased viability and potential efficacy of the testing drug.

2. The method of claim 1, wherein the plurality of target cells are a plurality of cancer cells.

3. The method of claim 1, wherein the testing drug is an anticancer drug.

4. The method of claim 3, wherein the anticancer drug is directed to a type of cancer represented by a plurality of cancer cells.

5. The method of claim 1, wherein a difference between the first amount of the culture media and the third amount of the culture media is approximately 100 µL.

6. The method of claim 1, further comprising a step of combining the microfluidic platform with a surface acoustic wave (SAW) sensor disposed beneath the microfluidic platform.

7. The method of claim 6, wherein an $IrO_2$ layer is deposited on a ZnO layer to increase sensitivity of the SAW sensor.

8. The method of claim 7, wherein surface acoustic wave generation of a potential-distributed wave at the $IrO_2$ layer is used to detect longitudinal pH measurements of the plurality of target cells.

* * * * *